(12) United States Patent
Miller et al.

(10) Patent No.: US 8,822,731 B2
(45) Date of Patent: Sep. 2, 2014

(54) SOLUBLE, PERSISTENT NONACENE DERIVATIVES

(75) Inventors: Glen P. Miller, Lee, NH (US); Irvinder Kaur, Durham, NH (US)

(73) Assignee: University of New Hampshire, Durham, NH (US)

( * ) Notice: Subject to any disclaimer, the term of this patent is extended or adjusted under 35 U.S.C. 154(b) by 598 days.

(21) Appl. No.: 12/627,800

(22) Filed: Nov. 30, 2009

(65) Prior Publication Data

US 2011/0130593 A1      Jun. 2, 2011

(51) Int. Cl.
*C07C 321/24* (2006.01)
*C07C 321/30* (2006.01)
*H01L 51/00* (2006.01)

(52) U.S. Cl.
CPC .......... *C07C 321/30* (2013.01); *H01L 51/0056* (2013.01)
USPC ................... 568/50; 568/38; 568/54; 568/34; 257/40

(58) Field of Classification Search
USPC ............... 568/57, 660, 34, 42, 48, 38, 50, 54; 257/40
See application file for complete search history.

(56) References Cited

U.S. PATENT DOCUMENTS

| | | | |
|---|---|---|---|
| 2,583,975 | A | 1/1952 | Tawney |
| 5,347,144 | A | 9/1994 | Garnier |
| 6,165,383 | A | 12/2000 | Chou |
| 6,265,243 | B1 | 7/2001 | Katz |
| H2084 | H | 10/2003 | Picciolo et al. |
| 6,690,029 | B1 | 2/2004 | Anthony |
| 7,276,395 | B2 | 10/2007 | Gerlach |
| 7,319,153 | B2 | 1/2008 | Vogel |
| 7,495,251 | B2 | 2/2009 | Zhu |
| 8,110,714 | B2 * | 2/2012 | Nagata et al. ................. 570/183 |
| 2006/0273311 | A1 | 12/2006 | Ohe |
| 2007/0137520 | A1 | 6/2007 | Brown |
| 2008/0113215 | A1 | 5/2008 | Kathirgamanathan |
| 2008/0191199 | A1 | 8/2008 | Anemian |
| 2008/0197325 | A1 | 8/2008 | Leeming |

FOREIGN PATENT DOCUMENTS

| | | | | |
|---|---|---|---|---|
| JP | 2000021571 A | | 1/2000 | |
| JP | 2004-256532 | * | 9/2004 | .............. C07C 15/20 |
| JP | 2004-339063 | * | 12/2004 | .............. C07C 5/367 |
| JP | 2006-335719 | * | 12/2006 | .............. C07C 25/22 |

OTHER PUBLICATIONS

Kaur et al; Journal of American Chemical Society, Feb. 25, 2009, 131, 3424-3425.*
Rogers, J.A., et al., Proc. Nat. Acad. Sci., 2001, 98:4835-4840.
Daniel, J.H., et al., ECS Transcations, 2006, 3:229-236.
Tunnell, A.J., et al., Org. Electron, 2008, 9:507-514.
Ono, K., et al., Tetrahedron, 2007, 61:9699-9704.
Palayangoda, S.S., et al., J. Org. Chem., 2007, 72:6584-6587.
Etienne, A. and C. Beauvios, Compt. Rend., 1954, 239:64-66.
Benor, A., et al., Org. Electron, 2007, 8:749-758.
Koch, N., et al., Org. Electron, 2006, 7:537-545.
Mondal, R., et al., Org. Letters 2007, 9, 2505-2508.
Mondal, R., et al., J. Amer. Chem. soc. 2006, 128, 9612-9613.
Bendikov, M., et al., J. Amer. Chem. Soc. 2004, 126, 7416-7417.
Anthony, J.E., Angew. Chem., Int. Ed. 2008, 47, 452-483.
Kaur, I., et al., J. Amer. Chem. Soc. 2008, 130, 16274-16286.
Peter Van Zant in Microchip Fabrication, Fourth Edition, McGraw-Hill, New York (2000).
Materials Research Society Symposium Proceedings v 558, Materials Research Society, Warrendale, PA,, USA, pp. 403-408 (2000).
Kaur, I., et al., "Exploiting Substituent Effects for the Synthesis of a Photooxidatively Resistant Heptacene Derivative", J. Am. Chem. Soc. 2009, 131: 3424-3425.
Chun, et al. "The Most Stable and Fully Characterized Functionalized Heptacene" Angew. Chem. Inst. Ed.; 2008, vol. 47; pp. 8380-8385.

* cited by examiner

*Primary Examiner* — Sudhakar Katakam
*Assistant Examiner* — Pancham Bakshi
(74) *Attorney, Agent, or Firm* — Pierce Atwood LLP; Kevin M. Farrell; David J. Wilson

(57) ABSTRACT

The present invention is directed towards a new class of semi-conducting nonacene derivatives. These compounds are all soluble species and they all possess superior resistance to oxidation as compared to their counterparts that lack the substitution patterns disclosed herein.

30 Claims, 23 Drawing Sheets

Figure 3

Location of bis(methylthio) substituents along the nonacene skeleton

Location of tetrakis(methylthio) substituents along the nonacene skeleton $M^+$ *m/z* 2188
$[M^+ - (OH)]$ *m/z* 2171

SOLUBLE, PERSISTENT NONACENE DERIVATIVES

The authors acknowledge the National Science Foundation (Nanoscale Science & Engineering Center for High-rate Nanomanufacturing, NSF-0425826) for financial support of this work. The Federal Government has a nonexclusive, non-transferable, irrevocable license in this invention on behalf of the United States. [37 CFR 401.14(b)].

BACKGROUND OF INVENTION

Traditionally, inorganic materials have dominated the electronic device industry. For example, silicon arsenide and gallium arsenide have been used as semiconductor materials, silicon dioxide has been used as an insulator material, and metals such as aluminum and copper have been used as electrode materials. In recent years, however, there has been an increasing research effort aimed at using organic materials rather than the traditional inorganic materials in electronic devices. Among other benefits, the use of organic materials may enable lower cost manufacturing of electronic devices, may enable large area applications, and may enable the use of flexible circuit supports for display backplane and integrated circuits.

Thin-film organic electronics promise lightweight, flexible, inexpensive devices produced using high rate, low cost, solution based methods like spin coating or reel-to-reel processing with compliant substrates (Rogers, J. A., et al., Proc. Nat. Acad. Sci., 2001, 98:4835-4840; Daniel, J. H., et al., ECS Tranactions, 2006, 3:229-236). In a low cost manufacturing environment, process steps like thermal annealing of thin-films to improve charge carrier mobilities (Tunnell, A. J., et al., Org. Electron, 2008, 9:507-514) should occur in air. Thus, it is important that the chosen organic semiconductor possesses both good solubility and excellent stability in air at elevated temperatures.

A variety of organic semiconductor materials have been considered, the most common being fused aromatic ring compounds as exemplified by small molecules such as pentacene-containing compounds, tetracene-containing compounds, anthracene-containing compounds, bis(acenyl)acetylene compounds, and acene-thiophene compounds. Several polymeric materials have also been considered such as regioregular polythiophenes, which are exemplified by poly(3-alkylthiophene), and polymers having fused thiophene units or bis-thiophene units.

Due to the high charge carrier mobilities associated with its thin films, pentacene is one of the most widely utilized organic semiconductor compounds. However, its application in thin-film electronic devices is hindered by its poor solubility and its propensity to photo-oxidize (Ono, K., et al., Tetrahedron, 2007, 61:9699-9704; Palayangoda, S. S., et al., J. Org. Chem., 2007, 72:6584-6587; Etienne, A. and C. Beauvios, Compt. Rend., 1954, 239:64-66; Benor, A., et al., Org. Electron, 2007, 8:749-758; Koch, N., et al., Org. Electron, 2006, 7:537-545). Pentacene oxidation leads to diminished electronic device performance. Pentacene-6,13-dione forms upon photooxidation and has been implicated as a deep charge carrier trap that reduces charge carrier mobility (Koch, N., et al., Org. Electron, 2006, 7:537-545). From a device perspective, larger acenes like hexacene, heptacene, octacene and nonacene are inherently more promising species. They have progressively smaller band gaps and potentially much higher charge carrier mobilities but they are also far more prone to oxidative degradation, a characteristic that has severely limited opportunities in OFET, OLED, OPV and other electronic applications. Thus, hexacene and heptacene have only been isolated in rigid polymeric matrices where they show lifetimes of approximately 12 and 4 hours, respectively. (See Mondal, R.; Adhikari, R. M.; Shah, B. K.; Neckers, D. C. Org. Letters 2007, 9, 2505-2508 and Mondal, R.; Shah, B. K.; Neckers, D. C. J. Amer. Chem. Soc. 2006, 128, 9612-9613.) Octacene and nonacene have never been isolated, nor have any of their derivatives. With its large size and predicted small HOMO-LUMO gap, nonacene in particular is a highly desirable—even if highly challenging—synthetic target. Unsubstituted (i.e., parent) nonacene is predicted to have open shell, singlet diradical, pi-conjugated ground state (Bendikov, M.; Houk, K. N.; Duong, H. M.; Starkey, K.; Carter, E. A.; Wudl, F. J. Amer. Chem. Soc. 2004, 126, 7416-7417) which indicates that even if formed, it would be a highly reactive species with a very short lifetime.

Therefore, what is needed in the art are substituted, soluble nonacene derivatives that possess improved oxidative resistance as compared to unsubstituted nonacene and that can be cast into thin-film organic semiconductor materials for use in electronic applications.

SUMMARY OF INVENTION

The present invention relates to novel and non-obvious organic semiconductor compounds. Presented herein, are embodiments of the present invention including novel and non-obvious nonacene-derived compounds that show surprising and exceptional oxidative resistance.

The present invention relates to a new class of semiconducting nonacene derivatives (organic semiconductor compound) with the general structures shown in FIG. 1. These compounds are all soluble species and they all possess superior resistance to oxidation as compared to their counterparts that lack the substitution patterns shown.

Acenes larger than hexacene (e.g., heptacene, octacene, nonacene), are known to have singlet diradical character which significantly diminishes their stability. Thus, Bendikov and co-workers described heptacene and larger acenes as singlet diradicals using unrestricted density functional theory (Bendikov, M.; Houk, K. N.; Duong, H. M.; Starkey, K.; Carter, E. A.; Wudl, F. J. Amer. Chem. Soc. 2004, 126, 7416-7417). As noted by Bendikov, the total spin, $<S^2>$, associated with large acenes increases down the series hexacene, heptacene, octacene, and nonacene, as does the difference in energy between the open shell singlet (preferred) and either the triplet or closed shell solutions. We surmise that the calculated total spin, $<S^2>$, associated with each acene should be closely linked to its rate of oxidative degradation. A stepwise diradical addition of either triplet oxygen, $^3O_2$, or singlet oxygen, $^1O_2$, will become increasingly facile with increasing total spin of the acene molecule. In the present invention, we have discovered that placement of alkylthio or arylthio substituents on the terminal rings of nonacene converts a species with singlet diradical character into a closed shell ground state species with vastly improved overall stability. For example, a nonacene derivative bearing 1, 2, 3, 4, 12, 13, 14, 15 arylthio substituents (Compound A of FIG. 2) is the first known example of a persistent nonacene derivative and is included in the present invention.

High level density functional theory (DFT) calculations indicate that many other non-obvious nonacene derivatives bearing any of the following alkylthio and/or arylthio substitution patterns will also have zero, near zero, approximately zero or essentially zero total spin, $<S^2>$, and thus show vastly improved stability: 1,4; 2,3; 1,4,13,14; 2,3,13,14; 1,2,3,4,12, 15; 1,2,3,4,13,14 and 1,2,3,4,12,13,14,15. The compounds of the present invention include all nonacene derivatives bearing any of these alkylthio and/or arylthio substitution patterns involving one or both terminal rings whether or not additional substituents are located at non-terminal rings. (See e.g., FIG. 1, compounds 1-12.) Additional stability may be gained by placing additional substituents on non-terminal rings at any of the following locations: C5, C6, C7, C8, C9, C10, C11, C16, C17, C18, C19, C20, C21, C22 (see, e.g., FIG. 1, compounds 1-12) and the present invention includes these compounds provided that alkylthio and/or arylthio substituents are also located at the aforementioned terminal ring positions such that the resulting derivative has zero, near zero or approximately zero total spin, $<S^2>$. When used herein, the terms "near zero," "approximately zero" and "essentially zero" are interchangeable and mean that the total spin is close enough to zero to permit the nonacene derivatives of the present invention to be stable or "persistent" in solution. In this regard, the calculated total spin, $<S^2>$, should be less than 0.1 and the term "persistent" is synonymous with the term "stable." A "stable" or "persistent" nonacene derivative is a nonacene derivative that has less than 50% oxidation after 1 hour when stored as a solution and directly exposed to ambient light and air.

For clarity, the accepted numbering scheme for nonacene is shown below:

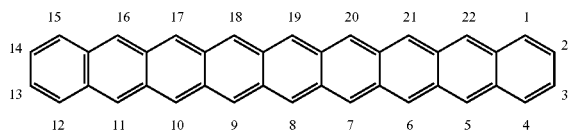 [SMILES: c1ccc2cc3cc4cc5cc6cc7cc8cc9ccccc9cc8cc7cc6cc5cc4cc3cc2c1]

Each number refers to a carbon atom on the nonacene skeleton where a substituent could be placed. Thus, for example, the number 8 refers to carbon 8 (or C8) where a substituent could be located.

With regards to the compounds shown in FIG. 1, R represents any functional group including, without limitation, hydrogen, alkyl moieties (e.g., methyl, ethyl, propyl, isopropyl, n-butyl-, isobutyl, sec-butyl, t-butyl, etc.), the nitrile group, the isonitrile group, carbonyl moieties of all types (e.g., ketones, esters, amides, anhydrides, etc.), alkene moieties, alkyne moieties, trialkylsilylethynyl moieties, aromatic moieties (e.g., phenyl and substituted phenyl groups including but not limited to o-dialkylphenyl, heteroaryl [e.g., thiophene and substituted thiophenes] of all types), the trifluoromethyl group, other perfluoroalkyl moieties, halogens (e.g., F, Cl, Br, I), alkylthio moieties (e.g., simple alkylthio groups including but not limited to decylthio as well as complex alkylthio moieties including but not limited to phenethylthio), and arylthio moieties.

With further regards to the compounds shown in FIG. 1, R preferably represents any functional group including alkyne moieties, trialkylsilylethynyl moieties, aromatic moieties (e.g., phenyl and substituted phenyl groups including but not limited to o -dialkylphenyl, heteroaryl [e.g., thiophene and substituted thiophenes] of all types), halogens (e.g., F, Cl, Br, I), alkylthio moieties (e.g., simple alkylthio groups including but not limited to decylthio as well as complex alkylthio moieties including but not limited to phenethylthio), and arylthio moieties.

Moreover, more than one type of the aforementioned functional groups may be present on a single compound (e.g., compound A of FIG. 2). In fact, multiple different functional groups may be present provided that alkylthio and/or arylthio substituents are also located at the aforementioned terminal ring positions such that the resulting derivative has zero, near zero or approximately zero total spin, $<S^2>$.

Closed shell ground states are desirable for stable, organic semiconductor compounds of the present invention. Thus, each compound of the present invention should have a DFT calculated total spin, $<S^2>$, of zero or approximately zero, as defined above.

BRIEF DESCRIPTION OF THE FIGURES

Figure 3:
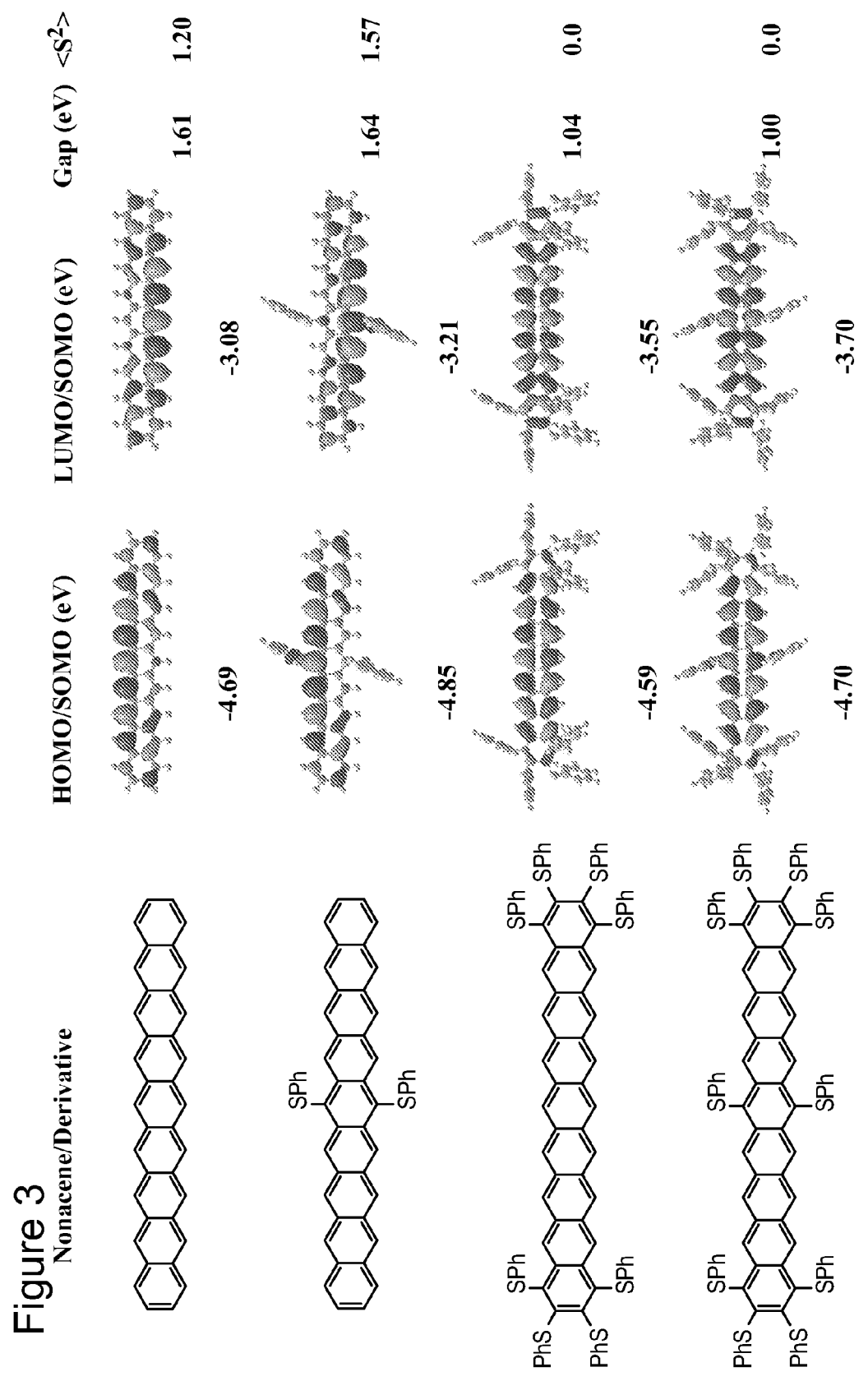

FIG. 3 shows HOMO, LUMO and SOMO orbitals and energies, associated HOMO-LUMO or SOMO-SOMO energy gaps, and total spin, $<S^2>$, for nonacene and three phenylthio substituted derivatives calculated at the UB3LYP/6-311+G**//B3LYP/6-31G* level of density functional theory. Note that the total spin, $<S^2>$, reaches zero for those compounds with arylthio substitution on the terminal rings.

DETAILED DESCRIPTION OF INVENTION

Compounds of the Present Invention

The compounds of the present invention are novel and non-obvious nonacene derivatives. Nonacenes are large acenes, a class of organic compounds and polycyclic aromatic hydrocarbons made up of linearly fused benzene rings. Nonacene contains nine linearly fused benzene rings. Although the structure of nonacene resembles that of smaller acenes like anthracene, tetracene and pentacene, neither nonacene nor any of its derivatives has ever been isolated, until now. As such, the properties of nonacene and its derivatives are poorly defined by those of skill in the art.

The compounds of the present invention are non-obvious nonacene derivatives bearing alkylthio and/or arylthio substituents at specified locations on the terminal rings such that the resulting nonacene derivatives have zero, near zero or approximately zero total spin, $<S^2>$, as calculated by density functional theory. Thus, the compounds of the present invention are non-obvious nonacene derivatives bearing alkylthio and/or arylthio substituents with any of the following substitution patterns: 1,4; 2,3; 1,4,13,14; 2,3,13,14; 1,2,3,4,12,15; 1,2,3,4,13,14 and 1,2,3,4,12,13,14,15. With zero, near zero or approximately zero calculated total spin, $<S^2>$, the nonacenes of the present invention show vastly improved stability as compared to unsubstituted (parent) nonacene. The alkyl groups referenced in the term "alkylthio substituents" of the present invention include all known alkyl moieties (e.g., standard alkyl groups like methyl, ethyl, propyl, isopropyl, n-butyl-, isobutyl, sec-butyl, t-butyl, etc., as well as complex alkyl groups like the phenethyl group or any other complex alkyl moiety in which an alkyl chain is tethered to a non-alkyl group or groups) attached as appropriate to a sulfur atom which is in turn directly attached to the nonacene skeleton. The aryl groups referenced in the term "arylthio substituents" of the present invention include all known aryl moieties (e.g., phenyl and substituted phenyl groups including but not limited to p-t-butylphenyl, heteroaryl groups including but not limited to thiophene and substituted thiophenes, and all other known aromatic groups) attached as appropriate to a sulfur atom which is in turn directly attached to the nonacene skeleton.

Figure 1:
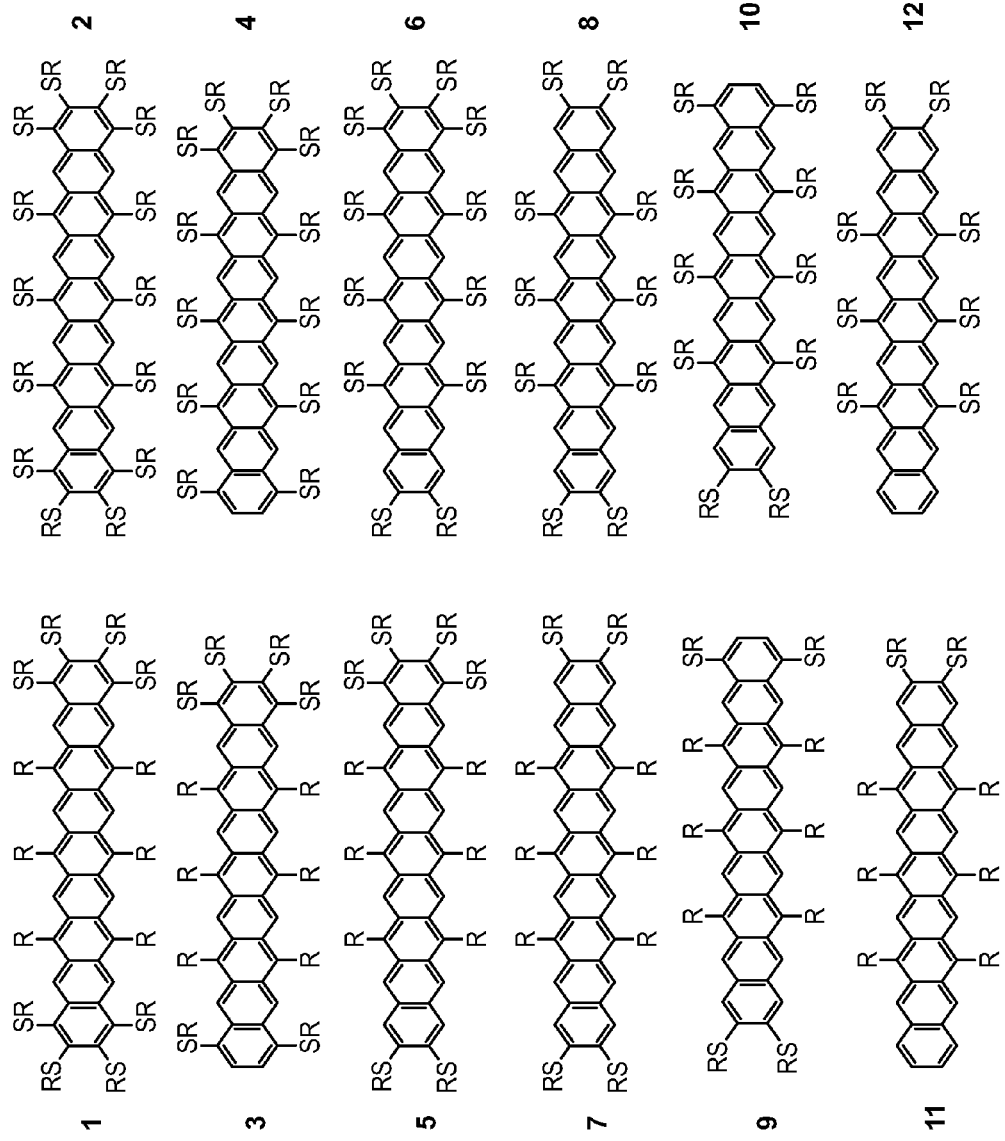
FIG. 1 shows a schematic representation of the generic compounds of the present invention.

FIG. 1 shows a schematic of the generic compounds of the present invention where R is selected from, without limitation, any group including hydrogen, alkyl moieties (e.g., methyl, ethyl, propyl, isopropyl, n-butyl-, isobutyl, sec-butyl, t-butyl, etc.), the nitrile group, the isonitrile group, carbonyl moieties of all types (e.g., ketones, esters, amides, anhydrides, etc.), alkene moieties, alkyne moieties, trialkylsilylethynyl moieties, aromatic moieties (e.g., phenyl and substituted phenyl groups including but not limited to o-dialkylphenyl, heteroaryl [e.g., thiophene and substituted thiophenes] of all types), the trifluoromethyl group, other perfluoroalkyl moieties, halogens (e.g., F, Cl, Br, I), alkylthio moieties (e.g., simple alkylthio groups including but not limited to decylthio as well as complex alkylthio moieties including but not limited to phenethylthio), and arylthio moieties. Moreover, more than one type of the aforementioned functional groups may be present on a single generic compound of the present invention. Multiple different functional groups may be present on a single generic compound of the present invention provided that alkylthio and/or arylthio substituents are also located at the 1,4; 2,3; 1,4,13,14; 2,3,13,14; 1,2,3,4,12,15; 1,2,3,4,13,14 or 1,2,3,4,12,13,14,15 terminal ring positions such that the resulting derivative has zero, near zero or approximately zero total spin, $<S^2>$, as calculated by density functional theory.

1,2,3,4,8,12,13,14,15,19-Deca(4'-t-butylphenylthio)-6,10,17,21-tetra(2',6'-dimethylphenyl)nonacene (Compound A of FIG. 2). Compound A of FIG. 2 has p-t-butylphenylthio (i.e., an arylthio group) substituents located at the 1,2,3,4,12,13,14,15 positions and is included in the present invention. The 1,2,3,4,12,13,14,15 placement of p-t-butylphenylthio groups effectively render the total spin, $<S^2>$, of the compound to be zero as calculated by density functional theory and as illustrated in FIG. 3. Additional p-t-butylphenylthio groups at the 8,19 positions and o-dimethylphenyl substituents at the 6,10,17, and 21 positions provide for enhanced oxidative resistance due to a combination of known electronic and steric substituent effects. (See, Kaur, I.; Jia, W.; Kopreski, R.; Selvarasah, S.; Dokmeci, M. R.; Pramanik, C.; McGruer, N. E. and Miller, G. P. *J. Amer. Chem. Soc.,* 2008, 130, 16274-16286.)

1,2,3,4,8,12,13,14,15,19-Deca(4'-t-butylphenylthio)nonacene (Compound B of FIG. 2). Compound B of FIG. 2 has p-t-butylphenylthio (i.e., an arylthio group) substituents located at the 1,2,3,4,12,13,14,15 positions and is included in the present invention. The 1,2,3,4,12,13,14,15 placement of p-t-butylphenylthio groups effectively render the total spin, $<S^2>$, of the compound to be zero as calculated by density functional theory and as illustrated in FIG. 3. Additional p-t-butylphenylthio groups at the 8,19 positions provide for enhanced oxidative resistance due to a known substituent effect. (See, Kaur, I.; Jia, W.; Kopreski, R.; Selvarasah, S.; Dokmeci, M. R.; Pramanik, C.; McGruer, N. E. and Miller, G. P. *J. Amer. Chem. Soc.,* 2008, 130, 16274-16286.).

Exemplary Uses of the Present Invention

Acenes, including large acenes, are useful as organic semiconductor materials in electronic devices. (See, Anthony, J. E. *Angew. Chem., Int. Ed.* 2008, 47, 452-483.) Likewise, the nonacene derivatives disclosed herein are useful as organic semiconductor materials in semiconductor devices. Although there are numerous types of semiconductor devices, common to all is the presence of one or more semiconductor materials. Semiconductor devices include, for example, rectifiers, transistors (of which there are many types including p-n-p, n-p-n and thin-film transistors), light emitting semiconductors devices (for example, organic light emitting diodes), photoconductors, current limiters, thermistors, p-n junctions, field-effect diodes, Scottky diodes and other devices known in the art. In each semiconductor device, the semiconductor material is combined with one or more conductors or insulators to form the device. Semiconductor devices can be prepared or manufactured by known methods such as, for example, those described by Peter Van Zant in *Microchip Fabrication*, Fourth Edition, McGraw-Hill, New York (2000).

Electronic devices include components such as, e.g., transistors, arrays of transistors, diodes, capacitors, embedded capacitors and resistors that are used to form circuits. Electronic devices also include, for example, arrays of circuits that perform an electronic function. Examples of these arrays or integrated circuits are amplifiers, receivers, transmitters and oscillators.

Applications of these devices and arrays include, for example, radio frequency identification devices (RFIDs), smart cards, lamps, displays and the like. The present invention is not limited by the type of the device.

Although the present invention is not limited by the manner in which it can be used as a semi-conductor material, a particularly useful type of transistor device, e.g., the thin-film transistor (TFT), generally includes a gate electrode, a gate dielectric on the gate electrode, a source electrode and a drain electrode adjacent to the gate dielectric, and a semiconductor layer adjacent to the gate dielectric and adjacent to the source and drain electrodes [see, for example, S. M. Sze, Physics of Semiconductor Devices, 2nd edition, John Wiley and Sons, page 492, New York (1981)]. These components can be assembled in a variety of configurations. More specifically, an organic thin-film transistor (OTFT) has an organic semiconductor layer.

Typically, a substrate supports the OTFT during manufacturing, testing, and/or use. Optionally, the substrate can provide an electrical function for the OTFT. Useful substrate materials include organic and inorganic materials. For example, the substrate can comprise inorganic glasses, ceramic foils, polymeric materials (for example, acrylics, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS), filled polymeric materials (for example, fiber-reinforced plastics (FRP)), and coated or uncoated metallic foils.

The gate electrode can be any useful conductive material. For example, the gate electrode can comprise doped silicon, or a metal, such as aluminum, chromium, gold, silver, nickel, palladium, platinum, tantalum, and titanium. Conductive polymers also can be used, for example polyaniline or poly (3,4-ethylenedioxythiophene)/poly(styrene sulfonate) (PEDOT:PSS). In addition, alloys, combinations, and multilayers of these materials can be useful. In some OTFTs, the same material can provide the gate electrode function and also provide the support function of the substrate. For example, doped silicon can function as the gate electrode and support the OTFT.

The gate dielectric is generally provided on the gate electrode. This gate dielectric electrically insulates the gate electrode from the balance of the OTFT device. Useful materials for the gate dielectric can comprise, for example, an inorganic electrically insulating material or a polymeric dielectric layer.

Specific examples of materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulfide. In addition, alloys, combinations, and multilayers of these materials can be used for the gate dielectric.

Alternatively, the gate dielectric may comprise an organic polymeric dielectric layer. A number of organic polymers have been considered as dielectric materials. These include polyimides, parylene C, crosslinked benzocyclobutene, and cyanoethylpullulan [see, for example, C. D. Sheraw, et al., "Spin-on polymer gate dielectric for high performance organic thin film transistors", Materials Research Society Symposium Proceedings v 558, Materials Research Society, Warrendale, Pa., USA, pages 403-408 (2000); U.S. Pat. No. 6,265,243 (Katz); and U.S. Pat. No. 5,347,144 (Garnier)].

The source electrode and drain electrode are separated from the gate electrode by the gate dielectric, while the organic semiconductor layer can be over or under the source electrode and drain electrode. The source and drain electrodes can be any useful conductive material. Useful materials include most of those materials described above for the gate electrode, for example, aluminum, barium, calcium, chromium, gold, silver, nickel, palladium, platinum, titanium, polyaniline, PEDOT:PSS, other conducting polymers, alloys thereof, combinations thereof, and multilayers thereof. Some of these materials are appropriate for use with n-type semiconductor materials and others are appropriate for use with p-type semiconductor materials, as is known in the art.

The thin film electrodes (that is, the gate electrode, the source electrode, and the drain electrode) can be provided by any useful means such as physical vapor deposition (for example, thermal evaporation or sputtering) or ink jet printing. The patterning of these electrodes can be accomplished by known methods such as shadow masking, additive photolithography, subtractive photolithography, printing, microcontact printing, and pattern coating.

One particularly useful method of preparing thin film transistors or integrated circuits is by means of a flexible, repositionable polymeric aperture masks to create integrated circuits or integrated circuit elements. The techniques involve sequentially depositing material through a number of polymeric aperture masks formed with patterns that define layers, or portions of layers, of the circuit. In some embodiments, circuits can be created solely using aperture mask deposition techniques, without requiring any of the etching or photolithography steps typically used to form integrated circuit patterns. The techniques can be particularly useful in creating circuit elements for electronic displays such as liquid crystal displays and low-cost integrated circuits such as radio frequency identification (RFID) circuits. In addition, the techniques can be advantageous in the fabrication of integrated circuits incorporating organic semiconductors, which typically are not compatible with photolithography or other wet processes.

In various embodiments, different repositionable aperture masks such as flexible aperture masks, free-standing aperture masks and polymeric aperture masks formed with patterns may be used to define a layer or a portion of a layer of an integrated circuit. Repositionable polymeric aperture masks may have a thickness of approximately between 5 and 50 microns or approximately between 15 and 35 microns. The various deposition apertures in the aperture masks may have widths less than approximately 1000 microns, less than approximately 50 microns, less than approximately 20 microns, less than approximately 10 microns, or even less than approximately 5 microns. Apertures of these sizes are particularly useful in creating small circuit elements for integrated circuits. Moreover, one or more gaps between deposition apertures may be less than approximately 1000 microns, less than approximately 50 microns, less than approximately 20 microns or less than approximately 10 microns, which is also useful in creating small circuit elements. Also, aperture masks that include a pattern having a width greater than approximately 1 centimeter, 25 centimeters, 100 centimeters, or even 500 centimeters are also described. Patterns having these widths can be useful in creating various circuits over a larger surface area as described in greater detail below. In some embodiments, layer may be deposited on a substrate through repositionable polymeric aperture masks.

Various laser ablation techniques may be used to facilitate the creation of polymeric aperture masks having patterns of deposition apertures. In addition, stretching techniques and other techniques may be used to facilitate alignment of flexible polymeric aperture masks. Furthermore, methods of controlling sag in aperture masks may be used which can be particularly useful in using masks that include a pattern that extends over a large width.

The aperture masks can provide a number of advantages. For example, the aperture masks can facilitate the creation of relatively small circuit elements using deposition processes. The aperture masks can facilitate circuit elements having widths less than approximately 1000 microns, less than approximately 50 microns, less than approximately 20 microns, less than approximately 10 microns, or even less than approximately 5 microns. Also, the aperture masks can facilitate the creation of relatively large circuit patterns, in some cases having circuit elements of the relatively small widths mentioned above that cover large areas (such as 10 square centimeters, 50 square centimeters, 1 square meter, or even larger areas). In addition, the aperture masks can reduce costs associated with circuit fabrication, and in the case of organic semiconductors, can even improve device performance. Polymeric aperture masks can be created using a laser ablation process that may be faster and less expensive than other techniques. Also, inexpensive polymeric materials can allow the polymeric masks to be disposable, although reusable embodiments are also described.

In addition, polymeric material may be well suited to be impregnated with magnetic material. In that case, the magnetic material may be used to reduce sag in the mask as described below. Furthermore, polymeric material is often stretchable, which allows the mask to be stretched to either reduce sag or to align the mask.

The compounds of the invention can be used alone or in combination as the organic semiconductor layer of the OTFT (or other semiconductor device). The layer can be provided by any useful means, such as, for example, vapor deposition and printing techniques.

The compounds of the invention can be used in integrated circuits comprising a plurality of OTFTs, as well as in various electronic articles. Such articles include, for example, radio-frequency identification (RFID) tags, backplanes for flexible displays (for use in, for example, personal computers, cell phones, or handheld devices), smart cards, memory devices, and the like.

The invention now being described, it will be apparent to one of ordinary skill in the art that many changes and modifications can be made thereto without departing from the spirit or scope of the invention.

As defined herein and as understood by those of ordinary skill in the art the art, HOMO and LUMO are acronyms for "Highest Occupied Molecular Orbital" and "Lowest Unoccupied Molecular Orbital," respectively. The difference of the energies of the HOMO and LUMO, termed the "HOMO-LUMO gap" for individual molecules and the "band gap" for collections of molecules in a thin-film can sometimes serve as a measure of the excitability of the molecule: the smaller the energy, the more easily it will be excited.

The HOMO level is to organic semiconductors and quantum dots what the valence band is to inorganic semiconductors. The same analogy exists between the LUMO level and the conduction band. The energy difference between the HOMO and LUMO level is approximately equal to the band gap energy.

When the molecule forms a dimer or an aggregate, the proximity of the orbitals of the different molecules induce a splitting of the HOMO and LUMO energy levels. This splitting produces vibrational sublevels which each have their own energy, slightly different from one another. There are as many vibrational sublevels as there are molecules that interact together. When there are enough molecules influencing each other (e.g., in an aggregate), there are so many sublevels that we no longer perceive their discrete nature: they form a continuum. We no longer consider energy levels, but energy bands. We no longer refer to the gap between filled and unfilled orbitals as the "HOMO-LUMO gap" but rather the "band gap".

EXEMPLIFICATION

Figure 4:
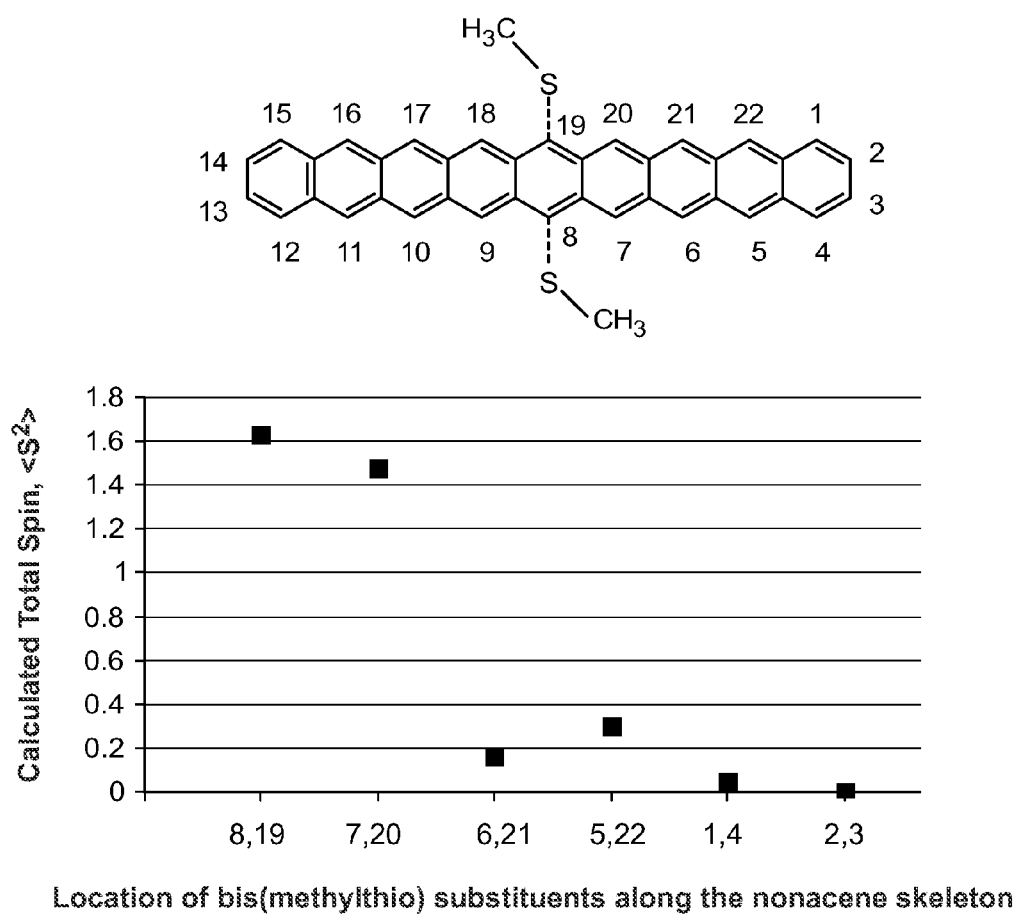
FIG. 4 shows the total spin, $<S^2>$, associated with several isomers of bis(methylthio)nonacene calculated at the UB3LYP/6-311+G**//B3LYP/6-31G* level of density functional theory. Note that the total spin, $<S^2>$, equals zero, near zero or approximately zero when the bis(methylthio) groups are located at either the 2, 3 or 1,4 positions, respectively, on a terminal ring, but that the total spin, $<S^2>$, is greater when the bis(methylthio) groups are located at the 5,22, 6,21, 7,20 or 8,19 positions on non-terminal rings.

In preparation for the synthesis of the exemplary compounds of the present invention, several isomers of bis(methylthio)nonacene calculated at the UB3LYP/6-311+G**//B3LYP/6-31G* level of density functional theory were considered to assess proof of concept. Note that the total spin, $<S^2>$, equals zero, near zero or approximately zero (as defined above) when the bis(methylthio) groups are located at either the 2, 3 or 1,4 positions, respectively, on a terminal ring, but that the total spin, $<S^2>$, is greater when the bis(methylthio) groups are located at the 5,22, 6,21, 7,20 or 8,19 positions on non-terminal rings. FIG. 4 shows the total spin, $<S^2>$, associated with these molecules.

Figure 5:
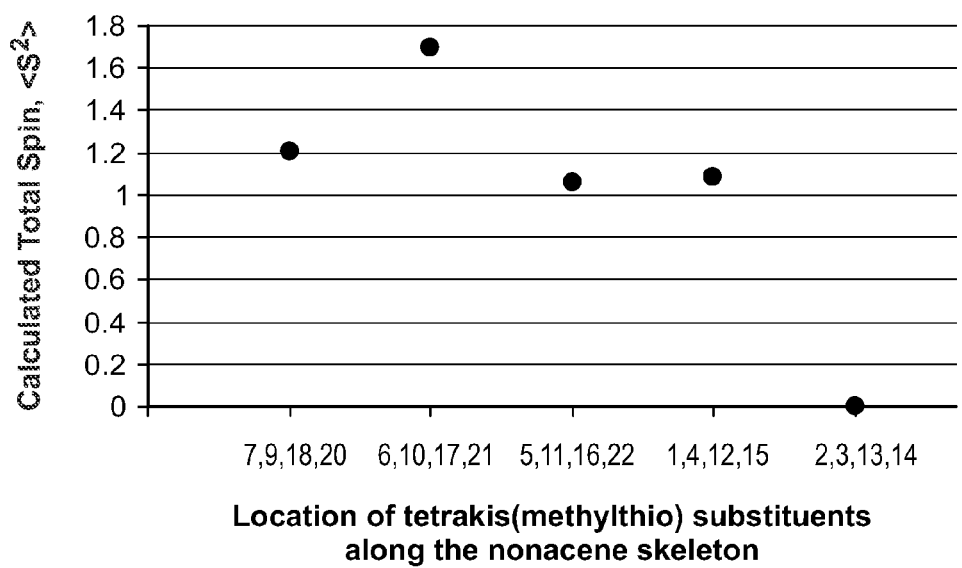
FIG. 5 shows the total spin, $<S^2>$, associated with several isomers of tetrakis(methylthio)nonacene calculated at the UB3LYP/6-311+G**//B3LYP/6-31G* level of density functional theory. Note that the total spin, $<S^2>$, equals zero, near zero or approximately zero when the tetrakis(methylthio) groups are located at the 2,3,13,14 positions of the two terminal rings, but that the total spin, $<S^2>$, is greater when the tetrakis(methylthio) groups are located at the 1,4,12,15, 5,11, 16,22, 6,10,17,21 and the 7,9,18,20 positions on non-terminal rings.

Likewise, several isomers of tetrakis(methylthio)nonacene calculated at the UB3LYP/6-311+G**//B3LYP/6-31G* level of density functional theory were considered to assess proof of concept. Note that the total spin, $<S^2>$, equals zero, near zero or approximately zero when the tetrakis(methylthio) groups are located at the 2,3,13,14 positions of the two terminal rings, but that the total spin, $<S^2>$, is greater when the tetrakis(methylthio) groups are located at the 1,4,12,15, 5,11, 16,22, 6,10,17,21 and the 7,9,18,20 positions on non-terminal rings. FIG. 5 shows the total spin, $<S^2>$, associated with these molecules.

Figure 2A:
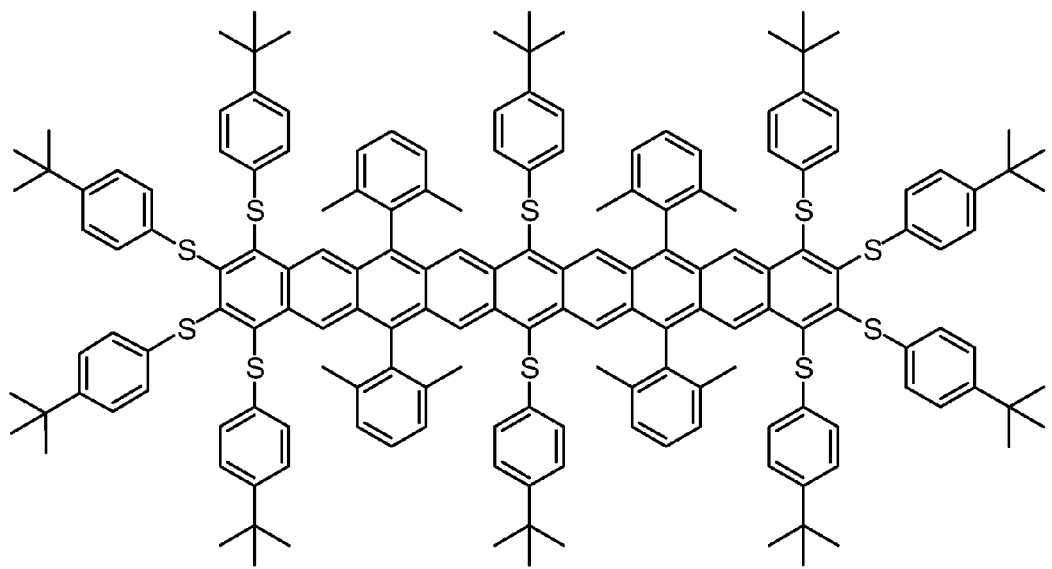
FIG. 2 shows compound A, the first known example of a persistent nonacene derivative, bearing 1, 2, 3, 4, 12, 13, 14, 15 arylthio substituents plus additional substituents, and compound B, a nonacene derivative bearing 1, 2, 3, 4, 12, 13, 14, 15 arylthio substituents plus additional 8,19 arylthio substituents that shows much greater stability than unsubstituted (parent) nonacene. Both compounds A and B are included in the present invention.
Figure 2B:
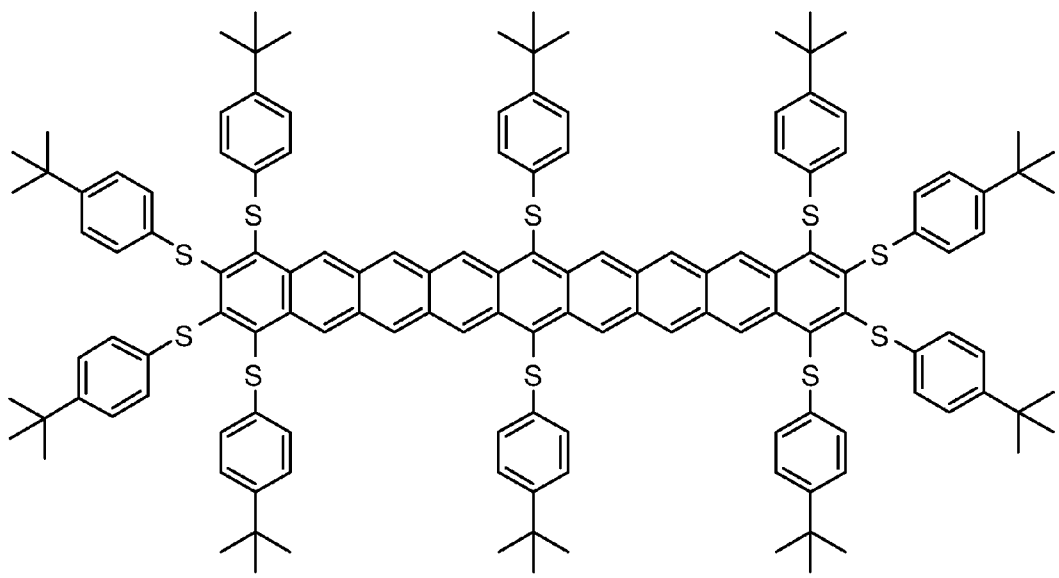
Figure 20:
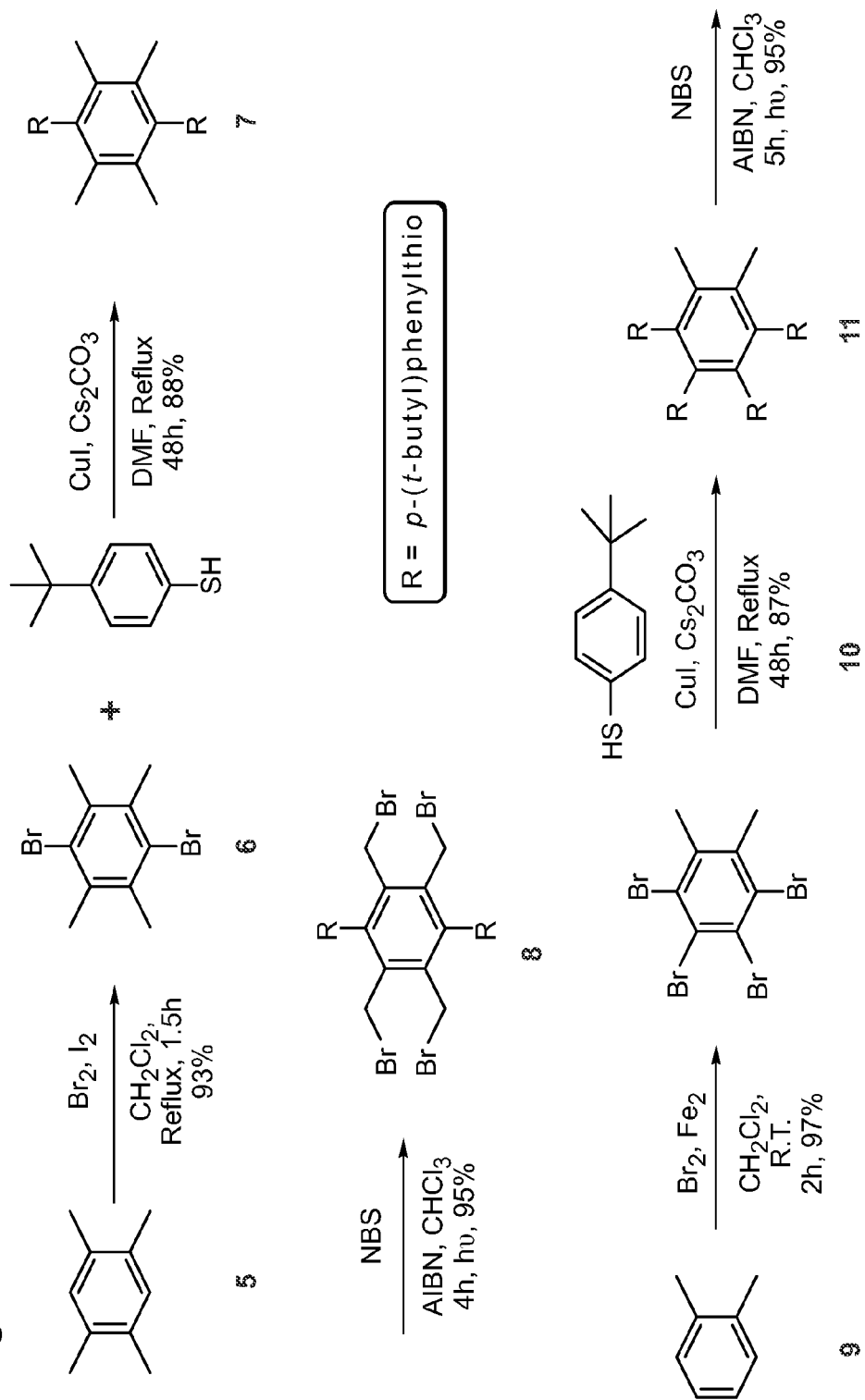
FIG. 20 shows a schematic diagram of the synthesis of 1,2,3,4,8,12,13,14,15,19-deca(4'-t-butylphenylthio)-6,10,17,21-tetra(2',6'-dimethylphenyl)nonacene, 1 (the compound of FIG. 2A), and 1,2,3,4,8,12,13,14,15,19-deca(4'-t-butylphenylthio)nonacene, 2 (the compound of FIG. 2B).
Figure 20:
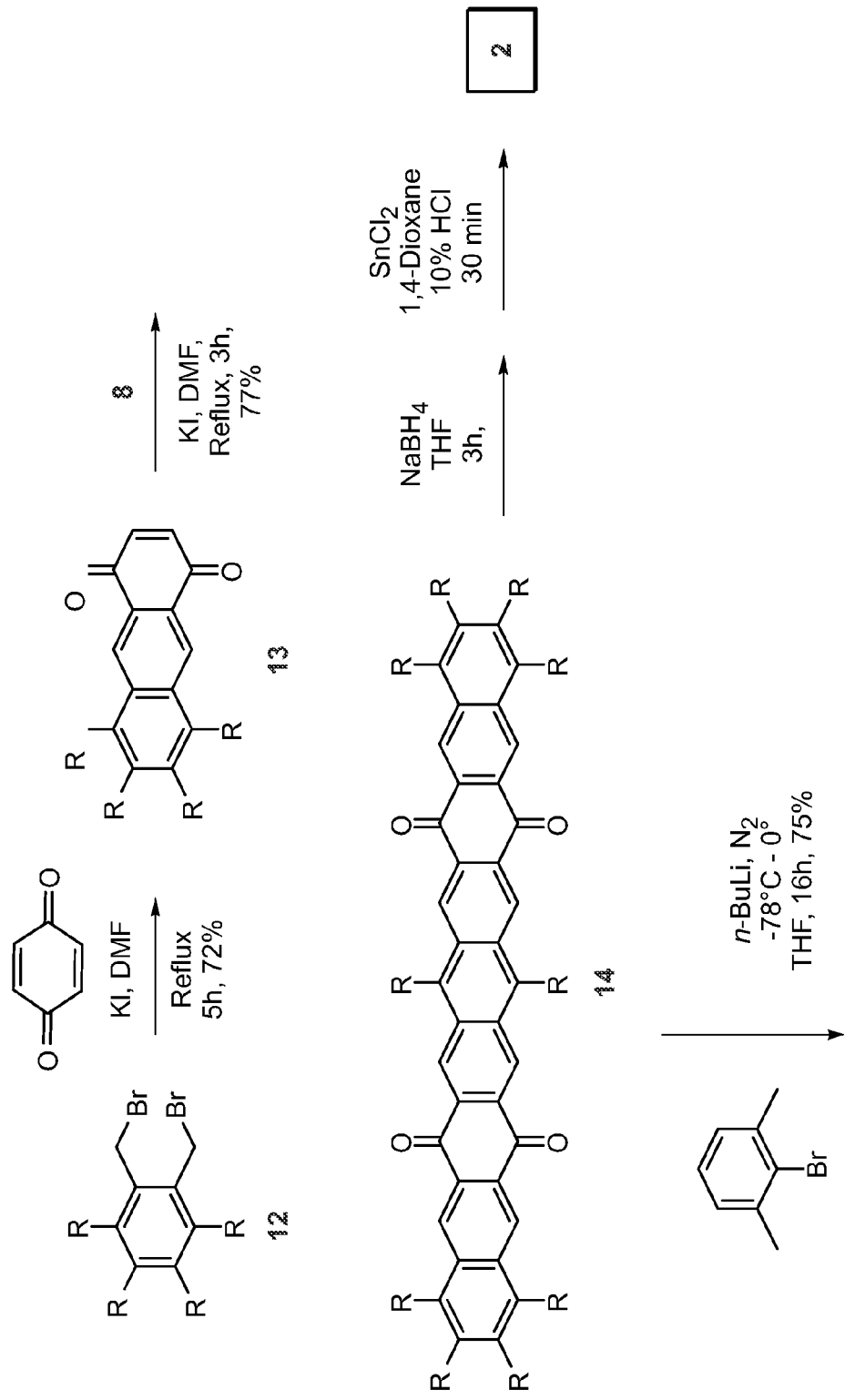
Figure 20:
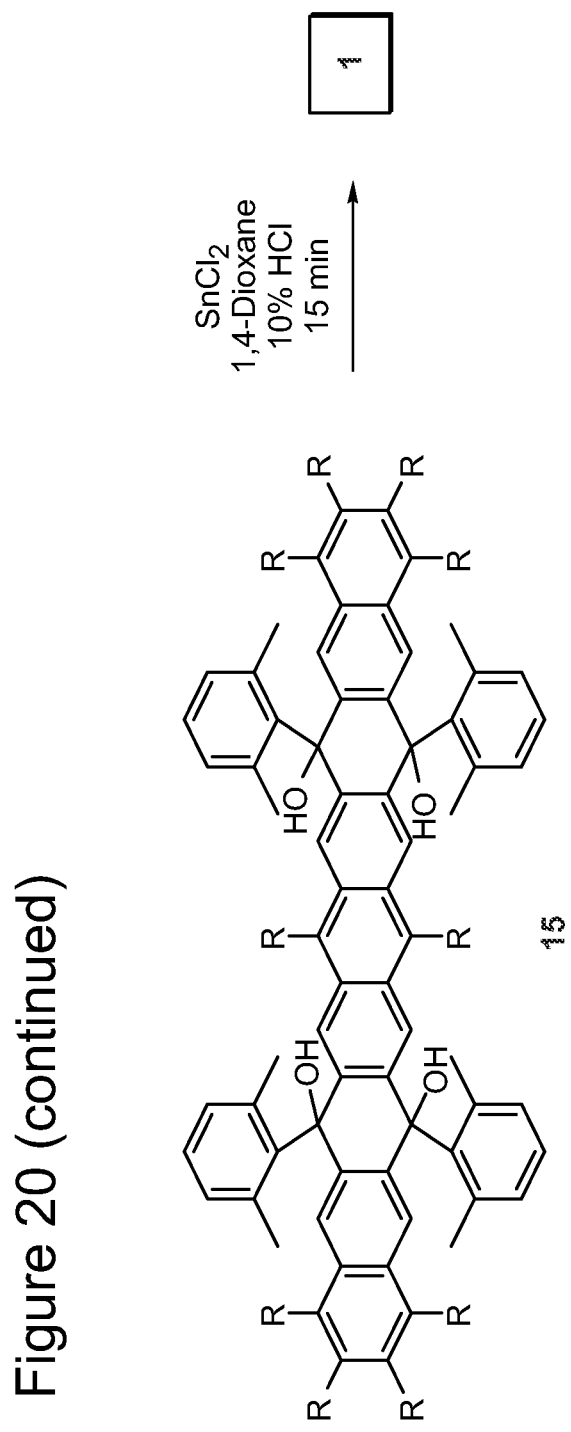

A schematic diagram of the synthesis procedure of two exemplary compounds of the present invention is shown in FIG. 20. 1,2,3,4,8,12,13,14,15,19-deca(4'-t-butylphenylthio)-6,10,17,21-tetra(2',6'-dimethylphenyl)nonacene is compound 1 (the structure of which is shown in FIG. 2A) and 1,2,3,4,8,12,13,14,15,19-deca(4'-t-butylphenylthio)nonacene is compound 2 (the structure of which is shown in FIG. 2B).

1,4-Dibromo-2,3,5,6-tetramethylbenzene

Figure 6:
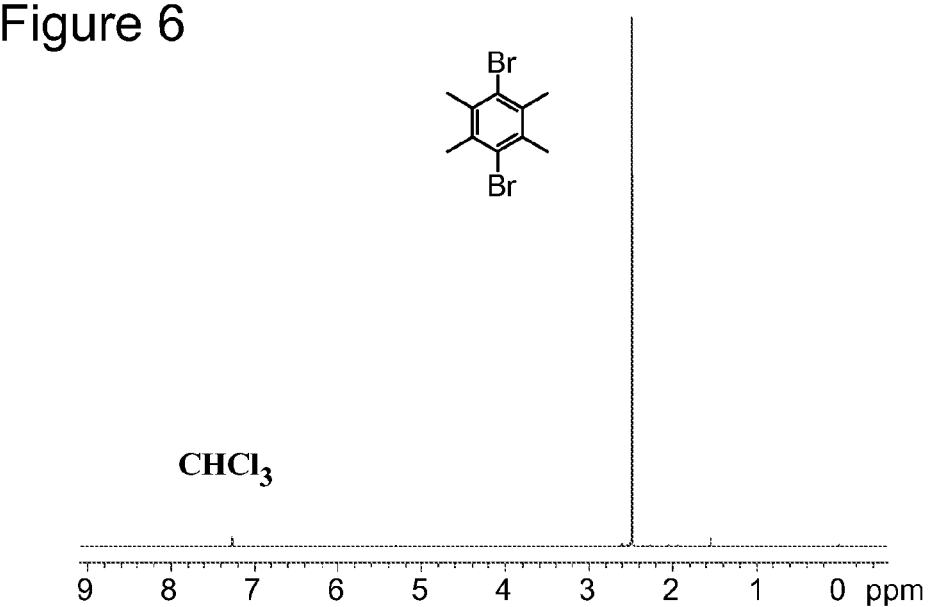
FIG. 6 shows the $^1H$ NMR spectrum of 1,4-dibromo-2,3, 5,6-tetramethylbenzene and the compound structure.

The reagent 1,2,4,5-tetramethylbenzene (25.0 g, 0.18 mol) was dissolved in 150 mL of dichloromethane. To this stirred solution was added $I_2$ (1.0 g, 3.94 mmol) followed by a slow dropwise addition of a solution of $Br_2$ (24 mL, 74.6 g, 0.47 mol) in 100 mL of dichloromethane. After the addition was complete, the resulting solution was heated to boiling for 1.5 hours. Upon cooling, 5M aq. NaOH (50 mL) was added to the reaction mixture. The product was collected by filtration, washed with $H_2O$ and dried to furnish 1,4-dibromo-2,3,5,6-tetramethylbenzene in 93% yield (50.6 g). $^1H$ NMR (500 MHz, $CDCl_3$): δ 2.48 (s, 12H). $^{13}C$ NMR (125.68 MHz, $CDCl_3$): δ 135.2, 128.3, 22.4. The $^1H$ NMR spectrum of 1,4-dibromo-2,3,5,6-tetramethylbenzene and the compound structure is shown in FIG. 6.

1,4-Bis(4'-t-butylphenylthio)-2,3,5,6-tetramethylbenzene

Figure 7:
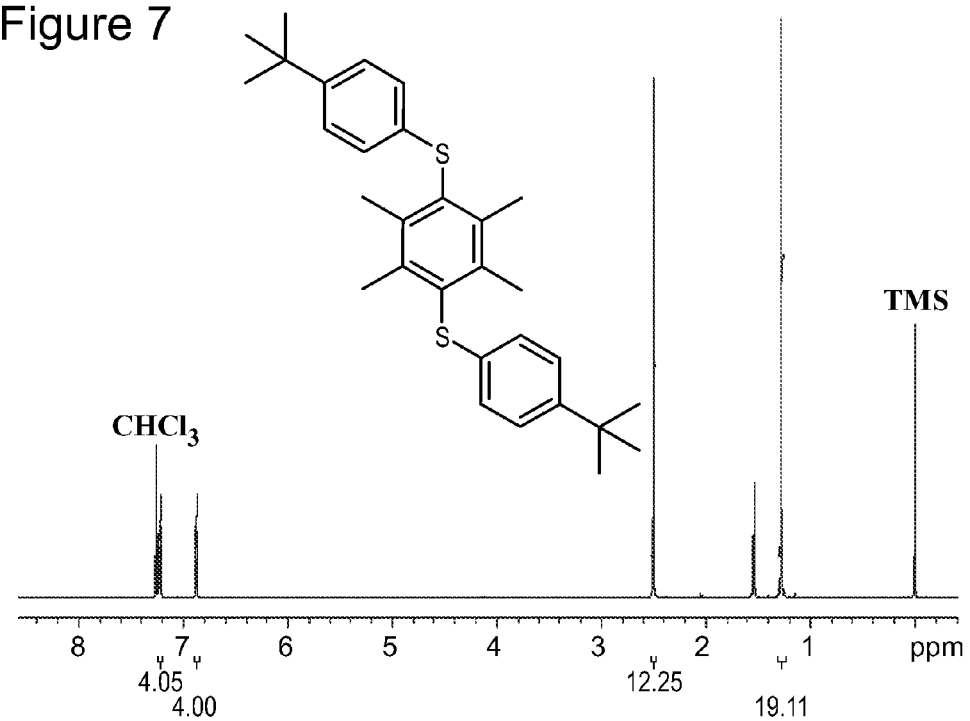
FIG. 7 shows the $^1H$ NMR spectrum of 1,4-bis(4'-t-butylphenylthio)-2,3,5,6-tetramethylbenzene and the compound structure.

To a solution of 1,4-dibromo-2,3,5,6-tetramethylbenzene (2.0 g, 6.85 mmol) and 4-t-butylthiophenol (2.6 g, 15.66 mmol) in dimethylformamide (60.0 mL) was added cesium carbonate (8.92 g, 27.38 mmol) and copper iodide (0.13 g, 0.068 mmol). The resulting suspension was heated to boiling for 2 days. Upon completion, the reaction mixture was cooled, filtered and extracted with ethyl acetate. The organic layer was separated and washed with water followed by brine and then dried to give the crude product which was further purified by column chromatography using hexanes:ethyl acetate (10:1) to furnish off-white solid product (2.78 g, 88% yield). $^1H$ NMR (500 MHz, $CDCl_3$): δ 7.23 (d, 4H, J=8.53 Hz), 6.87 (d, 4H, J=8.53 Hz), 2.50 (s, 12H), 1.28 (s, 18H). $^{13}C$ NMR (125.68 MHz, $CDCl_3$): δ 147.9, 140.5, 134.9, 133.4, 126.1, 125.8, 34.5, 31.5, 20.1. The $^1H$ NMR spectrum of 1,4-bis(4'-t-butylphenylthio)-2,3,5,6-tetramethylbenzene and the compound structure is shown in FIG. 7.

1,4-Bis(4'-t-butylphenylthio)-2,3,5,6-tetra(bromomethyl)benzene

Figure 8:
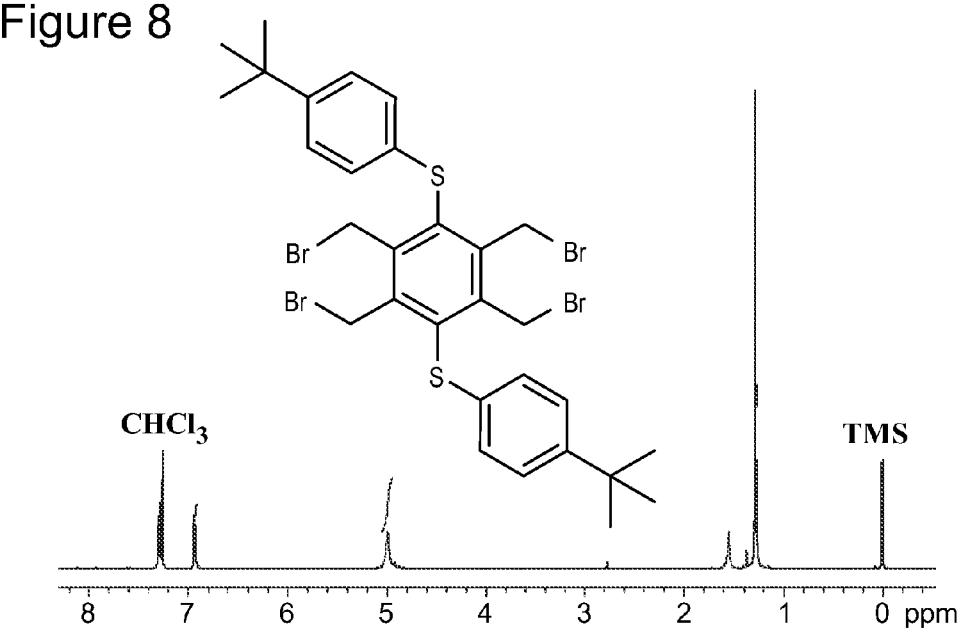
FIG. 8 shows the $^1H$ NMR spectrum of 1,4-bis(4'-t-butylphenylthio)-2,3,5,6-tetra(bromomethyl)benzene and the compound structure.

A mixture of 1,4-bis(4'-t-butylphenylthio)-2,3,5,6-tetramethylbenzene (1.0 g, 2.16 mmol) (Insert in FIG. 8), N-bromosuccinimide (1.92 g, 10.79 mmol) and AIBN (30 mg) in dry $CHCl_3$ (40.0 mL) was irradiated by a 250 W tungsten lamp for 4 h under reflux. After cooling, succinimide precipitated as a colorless powder and was filtered with $CHCl_3$ washing. Following evaporation of solvent from the filtrate, the crude product was suspended in MeOH (100 mL) and stirred for 5 min to dissolve unreacted NBS and by-products. The resulting suspension was filtered and the insoluble material was washed with MeOH to give the title compound (1.6 g, 95%) as a white solid. $^1H$ NMR (500 MHz, $CDCl_3$): δ 7.29 (d, 4H, J=8.58 Hz), 6.93 (d, 4H, J=8.58 Hz), 4.99 (bs, 8H), 1.28 (s, 18H). $^{13}C$ NMR (125.68 MHz, $CDCl_3$): δ 149.7, 144.7, 137.2, 132.4, 126.7, 126.4, 34.6, 31.4, 29.1. The $^1H$ NMR spectrum of 1,4-bis(4'-t-butylphenylthio)-2,3,5,6-tetra(bromomethyl)benzene and the compound structure is shown in FIG. 8.

1,2,3,4-Tetrabromo-5,6-dimethylbenzene

Figure 9:
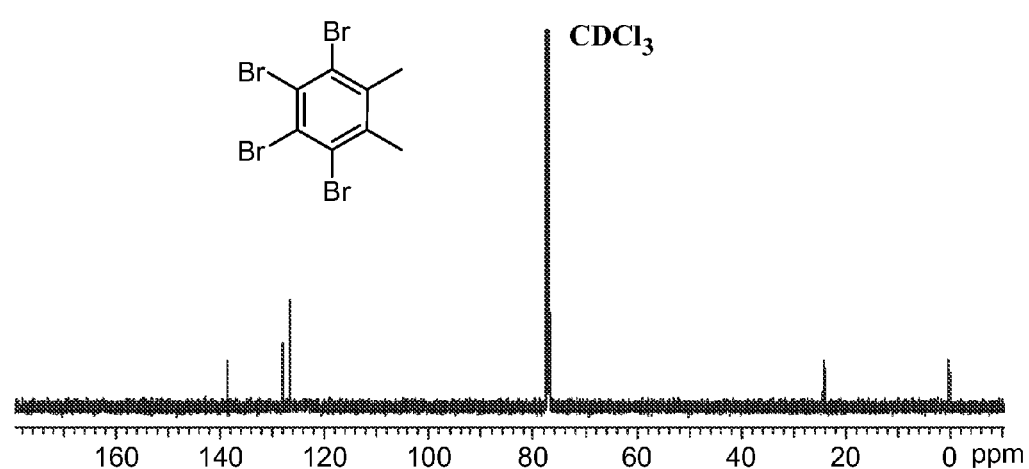
FIG. 9 shows the $^{13}C$ NMR spectrum of 1,2,3,4-tetrabromo-5,6-dimethylbenzene and the compound structure.

To a stirred solution of o-xylene (20.0 g, 0.19 mol) in 150 mL of dichloromethane kept at 0° C. was added iron fillings (2.26 g, 0.04 mol) followed by a slow, dropwise addition of a solution of $Br_2$ (82.0 mL, 256.12 g, 1.6 mol) in 100 mL of dichloromethane for 1 h. After the addition was complete, the resulting solution was stirred at room temp for 1 h. Water (200 mL) was added to the reaction mixture and the product was collected by filtration, washed with 3% sodium bicarbonate solution, 5N HCl and methanol, in succession. The product was dried to furnish 1,2,3,4-tetrabromo-5,6-dimethylbenzene in 97% yield (77.23 g). $^1H$ NMR (500 MHz, $CDCl_3$): δ 2.55 (s, 6H). $^{13}C$ NMR (125.68 MHz, $CDCl_3$): δ 138.6, 127.9, 126.5, 24.2. The $^{13}C$ NMR spectrum of 1,2,3,4-tetrabromo-5,6-dimethylbenzene and the compound structure is shown in FIG. 9.

1,2,3,4-Tetra(4'-t-butylphenylthio)-5,6-dimethylbenzene

Figure 10A:
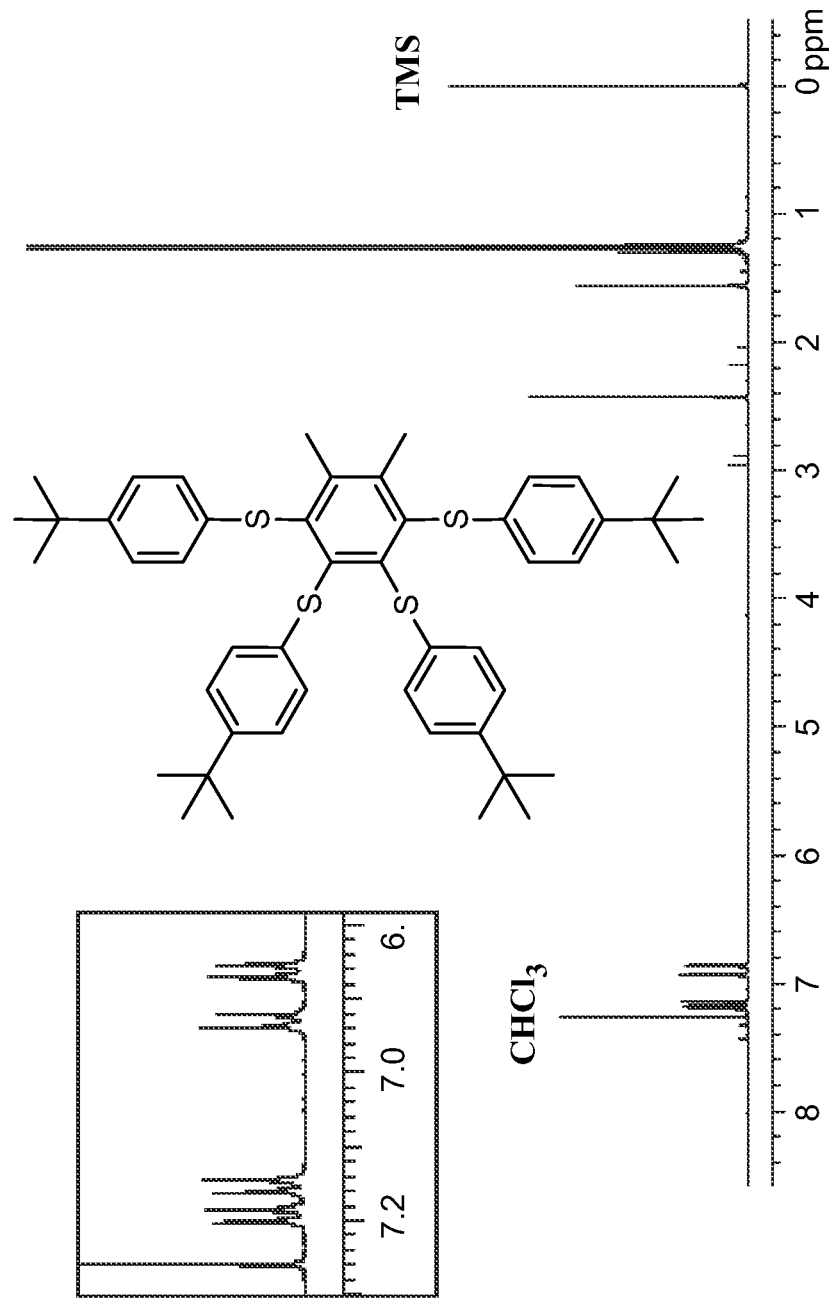
FIGS. 10A & B show the $^1H$ (FIG. 10A) and $^{13}C$ NMR (FIG. 10B) spectra for 1,2,3,4-tetra(4'-t-butylphenylthio)-5, 6-dimethylbenzene and the compound structure.
Figure 10B:
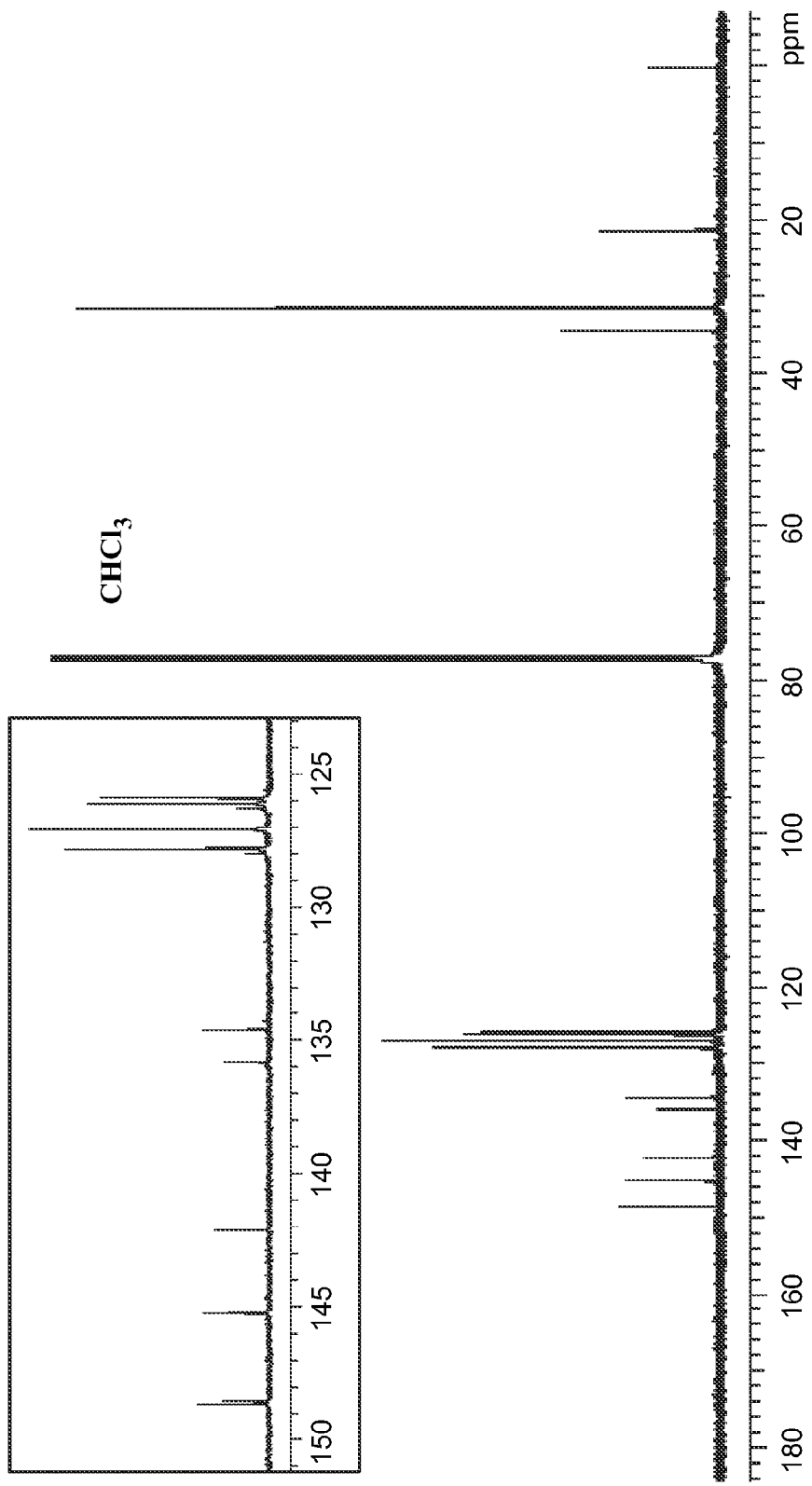

To a solution of 1,2,3,4-tetrabromo-5,6-dimethylbenzene (2.0 g, 4.74 mmol) and 4-t-butylthiophenol (4.73 g, 28.44 mmol) in dimethylformamide (40.0 mL) was added cesium carbonate (13.00 g, 39.89 mmol) and copper iodide (0.36 g, 0.19 mmol). The resulting suspension was heated to boiling for 2 days. Upon completion, the reaction mixture was cooled, filtered and extracted with ethyl acetate. The organic layer was separated and washed with water and brine and then dried to give a crude product that was further purified by column chromatography using hexanes:ethyl acetate (9:1) as eluant to furnish the off-white solid product (3.14 g, 87% yield). $^1H$ NMR (500 MHz, $CDCl_3$): δ 7.19 (d, 4H, J=8.54 Hz), 7.15 (d, 4H, J=8.54 Hz), 6.93 (d, 4H, J=8.78 Hz), 6.86 (d, 4H, J=8.78 Hz), 2.43 (s, 6H), 1.27 (s, 18H), 1.24 (s, 18H). $^{13}C$ NMR (125.68 MHz, $CDCl_3$): δ 148.7, 148.6, 145.3, 145.2, 142.1, 135.8, 134.6, 127.8, 127.0, 126.1, 125.9, 34.53, 34.49, 31.5, 21.4. The $^1H$ and $^{13}C$ NMR spectra for 1,2,3,4-tetra(4'-t-butylphenylthio)-5,6-dimethylbenzene and the compound structure are shown in FIGS. 10A & B.

1,2,3,4-Tetra(4'-t-butylphenylthio)-5,6-bis(bromomethyl)benzene

Figure 11:
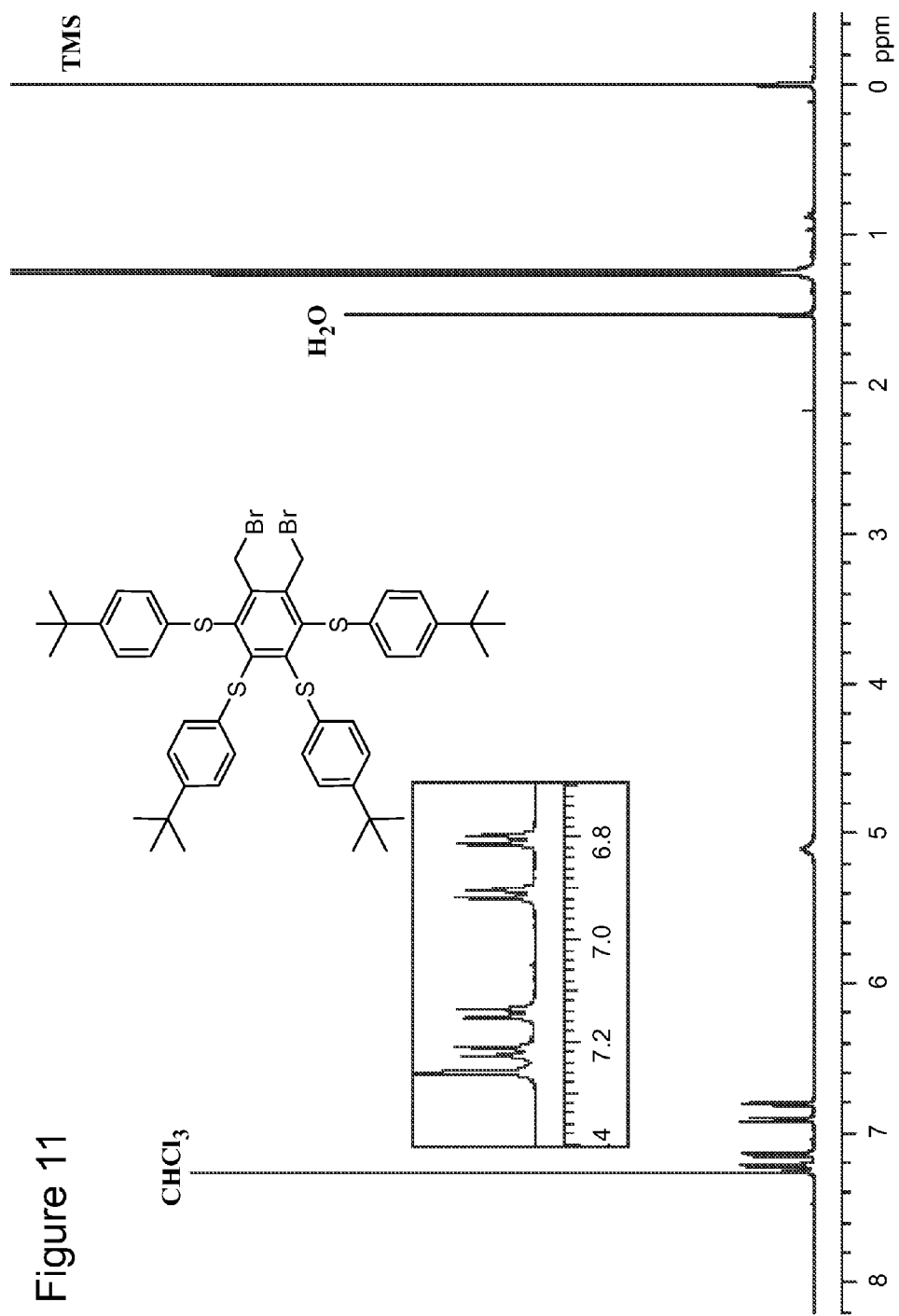
FIG. 11 shows the $^1H$ NMR spectrum of 1,2,3,4-tetra(4'-t -butylphenylthio)-5,6-bis(bromomethyl)benzene and the compound structure.

A suspension of 1,2,3,4-tetra(4'-t-butylphenylthio)-5,6-dimethylbenzene (2.0 g, 2.62 mmol), N-bromosuccinimide (2.0 g, 11.24 mmol) and AIBN (0.05 g) in dry $CHCl_3$ (50.0 mL) was irradiated by a 250 W tungsten lamp for 5 h under reflux. After cooling, succinimide precipitated as a colorless powder and was filtered with $CHCl_3$ washing. Following evaporation of solvent from the filtrate, the crude product was suspended in MeOH (100 mL) and stirred for 5 min to remove unreacted NBS and by-products. The resulting suspension was filtered and the insoluble material was washed with MeOH to give the title compound (2.29 g, 95%) as a white solid. $^1H$ NMR (500 MHz, $CDCl_3$): δ 7.22 (d, 4H, J=8.3 Hz), 7.14 (d, 4H, J=8.3 Hz), 6.91 (d, 4H, J=8.3 Hz), 6.80 (d, 4H, J=8.3 Hz), 5.10 (bs, 4H), 1.27 (s, 18H), 1.24 (s, 18H). $^{13}C$ NMR (125.68 MHz, $CDCl_3$): δ 150.4, 149.4, 149.3, 143.8, 143.3, 134.7, 133.7, 128.0, 127.3, 126.3, 125.9, 34.58, 34.55, 31.5, 30.3. A $^1H$ NMR spectrum of 1,2,3,4-tetra(4'-t-butylphenylthio)-5,6-bis(bromomethyl)benzene and the compound structure is shown in FIG. 11.

5,6,7,8-Tetra(4'-t-butylphenylthio)anthracene-1,4-dione

Figure 12:
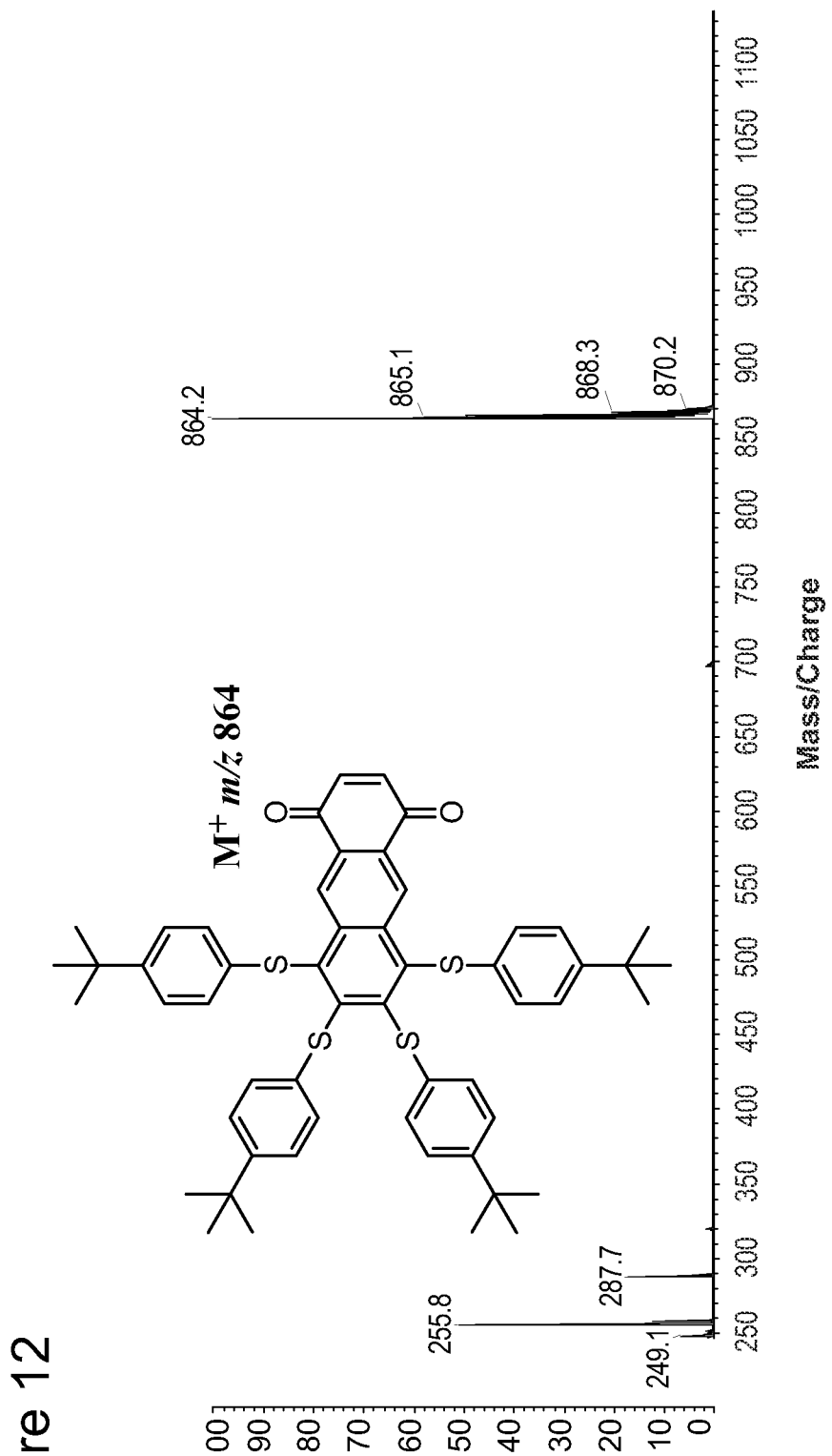
FIG. 12 shows the laser desorption ionization mass spectrum (LDI-MS) of 5,6,7,8-tetra(4'-t-butylphenylthio)anthracene-1,4-dione and the compound structure.

To a clear solution of 1,2,3,4-tetra(4'-t-butylphenylthio)-5,6-bis(bromomethyl)benzene (1.0 g, 1.09 mmol) in DMF (20 mL) was added 1,4-benzoquinone (0.15 g, 1.39 mmol) and KI (1.08 g, 6.5 mmol). The resulting reddish brown suspension was heated and stirred at 155° C. for 5 h. After cooling to RT, the yellow solids were vacuum filtered, washed with water and acetone, and finally dried to yield the product (0.68 g, 72%). $^1$H NMR (500 MHz, CDCl$_3$): δ 9.40 (s, 2H), 7.18 (d, 4H, J=8.54 Hz), 7.17 (d, 4H, J=8.54 Hz), 7.01 (s, 2H), 7.00 (d, 4H, J=8.54 Hz), 6.93 (d, 4H, J=8.54 Hz), 1.25 (s, 18H), 1.23 (s, 18H). $^{13}$C NMR (125.68 MHz, CDCl$_3$): δ 184.1, 150.0, 149.8, 143.1, 140.1, 138.0, 137.6, 134.8, 133.8, 129.7, 129.7, 128.7, 128.4, 126.4, 126.2, 34.61, 34.59, 31.42, 31.36. LDI-MS m/z: 864 [M$^+$]. The laser desorption ionization mass spectrum (LDI-MS) of 5,6,7,8-tetra(4'-t-butylphenylthio)anthracene-1,4-dione and the compound structure is shown in FIG. 12.

1,2,3,4,8,12,13,14,15,19-Deca(4'-t-butylphenylthio)nonacene-6,10,17,21-tetraone

Figure 13:
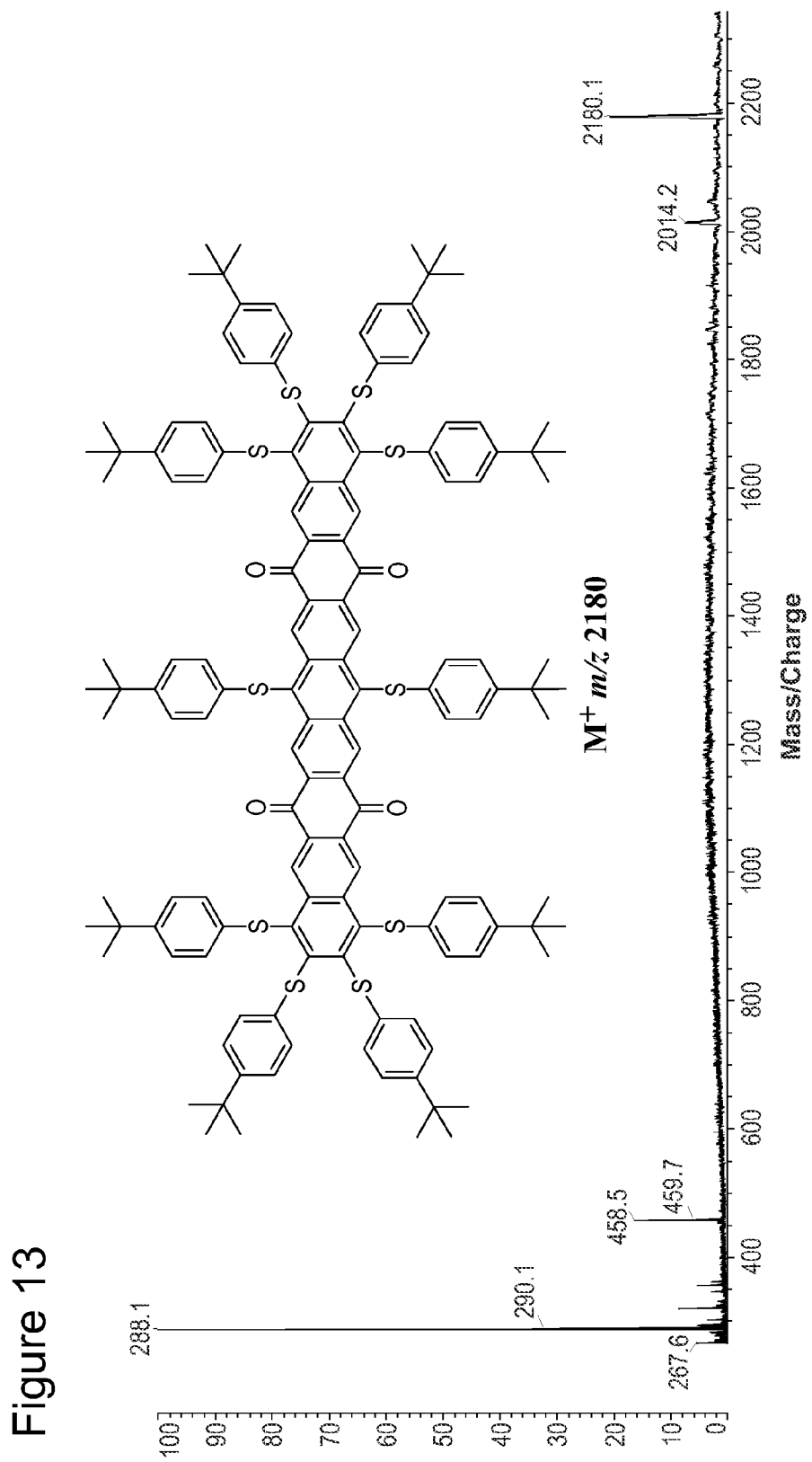
FIG. 13 shows the laser desorption ionization mass spectrum (LDI-MS) of 1,2,3,4,8,12,13,14,15,19-deca(4'-t-butylphenylthio)nonacene-6,10,17,21-tetraone and the compound structure.

To a clear solution of 1,4-bis(4'-t-butylphenylthio)-2,3,5,6-tetra(bromomethyl)benzene (0.138 g, 0.177 mmol) in DMF (10 mL) was added 5,6,7,8-tetra(4'-t-butylphenylthio)anthracene-1,4-dione (0.322 g, 0.372 mmol) and potassium iodide (0.48 g, 2.89 mmol). The resulting reddish brown suspension was heated and stirred at 155° C. for 3 h. After cooling to RT, the yellow solids were vacuum filtered and washed with water and acetone followed by drying to yield the desired product (0.29 g, 77%). $^1$H NMR (500 MHz, CDCl$_3$): δ 10.12 (s, 4H), 9.70 (s, 4H), 7.19 (d, 16H, J=8.3 Hz), 7.06 (d, 16H, J=8.3 Hz), 6.95 (d, 8H, J=8.3 Hz), 1.25 (s, 54H), 1.21 (s, 36H). LDI-MS m/z: 2180 [M$^+$]. The laser desorption ionization mass spectrum (LDI-MS) of 1,2,3,4,8,12,13,14,15,19-deca(4'-t-butylphenylthio)nonacene-6,10,17,21-tetraone and the compound structure is shown in FIG. 13.

Figure 14A:
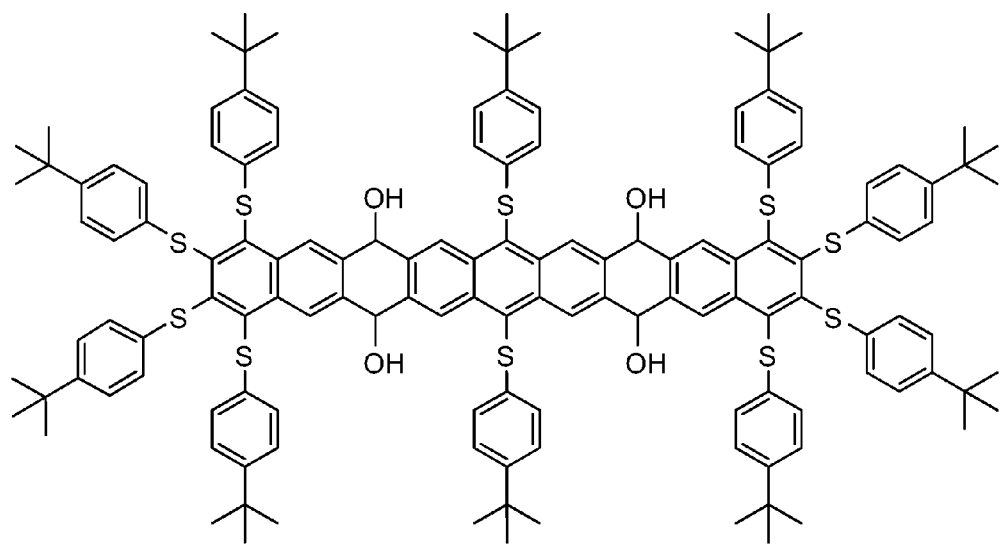
FIGS. 14A & B show the laser desorption ionization mass spectrum (LDI-MS) of 1,2,3,4,8,12,13,14,15,19-deca(4'-t-butylphenylthio)-6, 10,17,21-tetrahydrononacene-6,10,17,21-tetraol (FIG. 14B) and the compound structure (FIG. 14A).
Figure 14B:
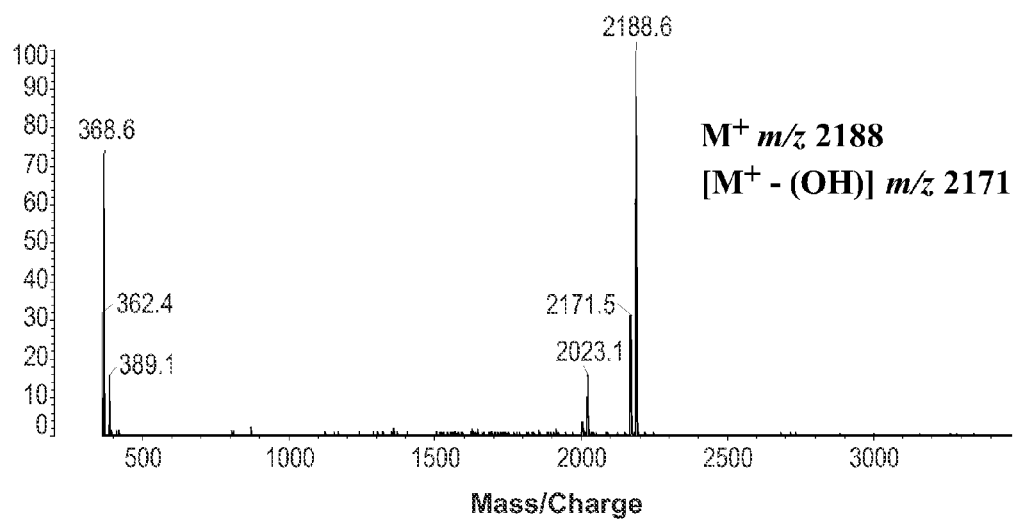

1,2,3,4,8,12,13,14,15,19-Deca(4'-t-butylphenylthio)-6,10,17,21-tetrahydrononacene-6,10,17,21-tetraol To a suspension of 1,2,3,4,8,12,13,14,15,19-deca(4'-t-butylphenylthio)nonacene-6,10,17,21-tetraone (0.5 g, 0.23 mmol) in dry THF (10 mL) under a N$_2$ atmosphere was slowly added NaBH$_4$ (0.1 g, 2.64 mmol). The reaction mixture was stirred at room temp for 3 h, and then quenched with H$_2$O. The resulting mixture was filtered, washed with H$_2$O, and dried in vacuo to give the desired product as a light yellow solid (0.47 g, 94%). LDI-MS m/z: 2188 [M$^+$], 2171 [M$^+$-OH]. The laser desorption ionization mass spectrum (LDI-MS) of 1,2,3,4,8,12,13,14,15,19-deca(4'-t-butylphenylthio)-6,10,17,21-tetrahydrononacene-6,10,17,21-tetraol is shown in FIG. 14B. The compound structure is shown in FIG. 14A.

Figure 15A:
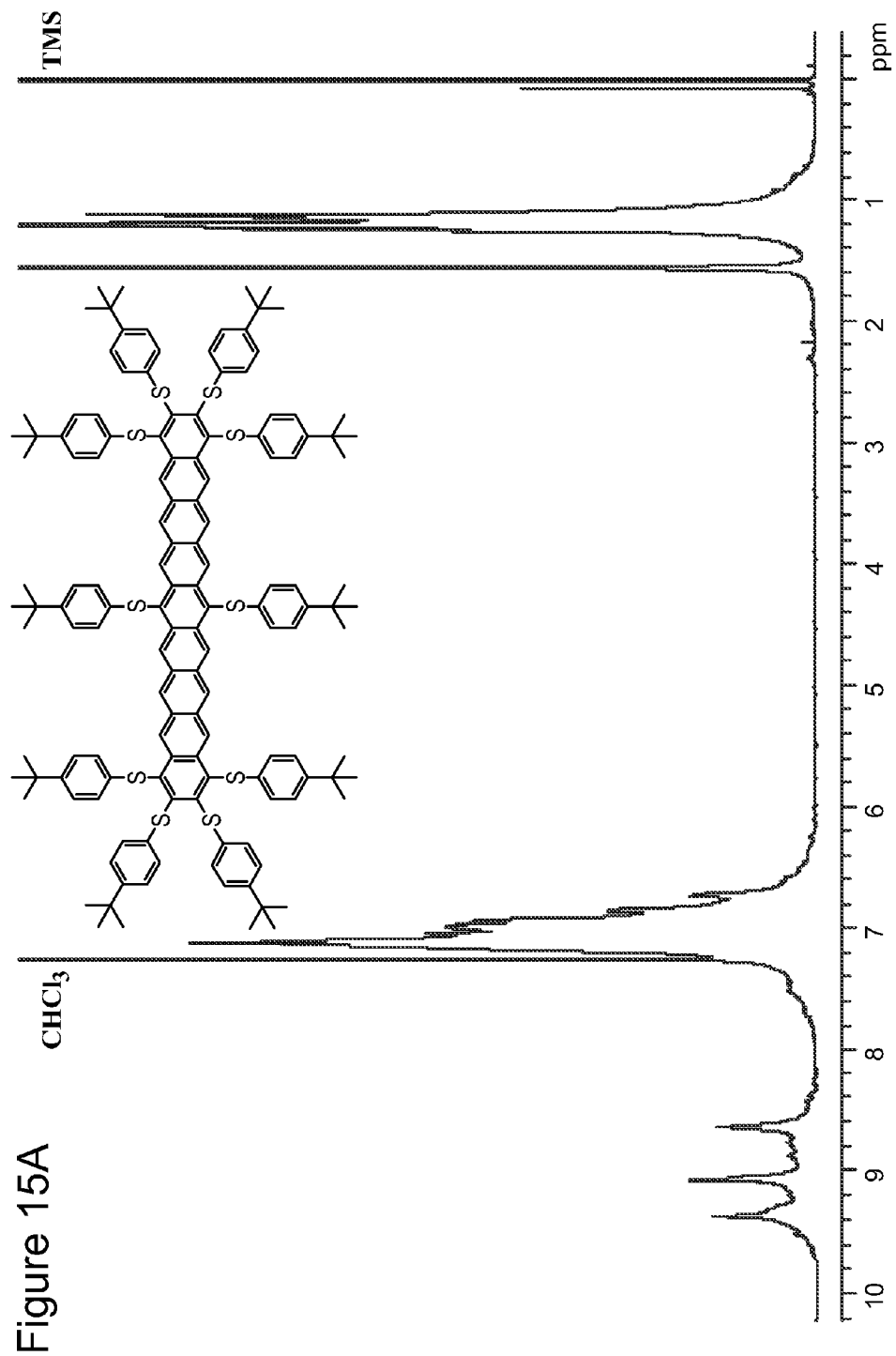
FIGS. 15A & B show the $^1$H NMR spectrum (FIG. 15$^a$) and laser desorption ionization mass spectrum (LDI-MS) (FIG. 15B) for 1,2,3,4,8,12,13,14,15,19-deca(4'-t-butylphenylthio)nonacene. The compound structure is shown in FIG. 15A.
Figure 15B:
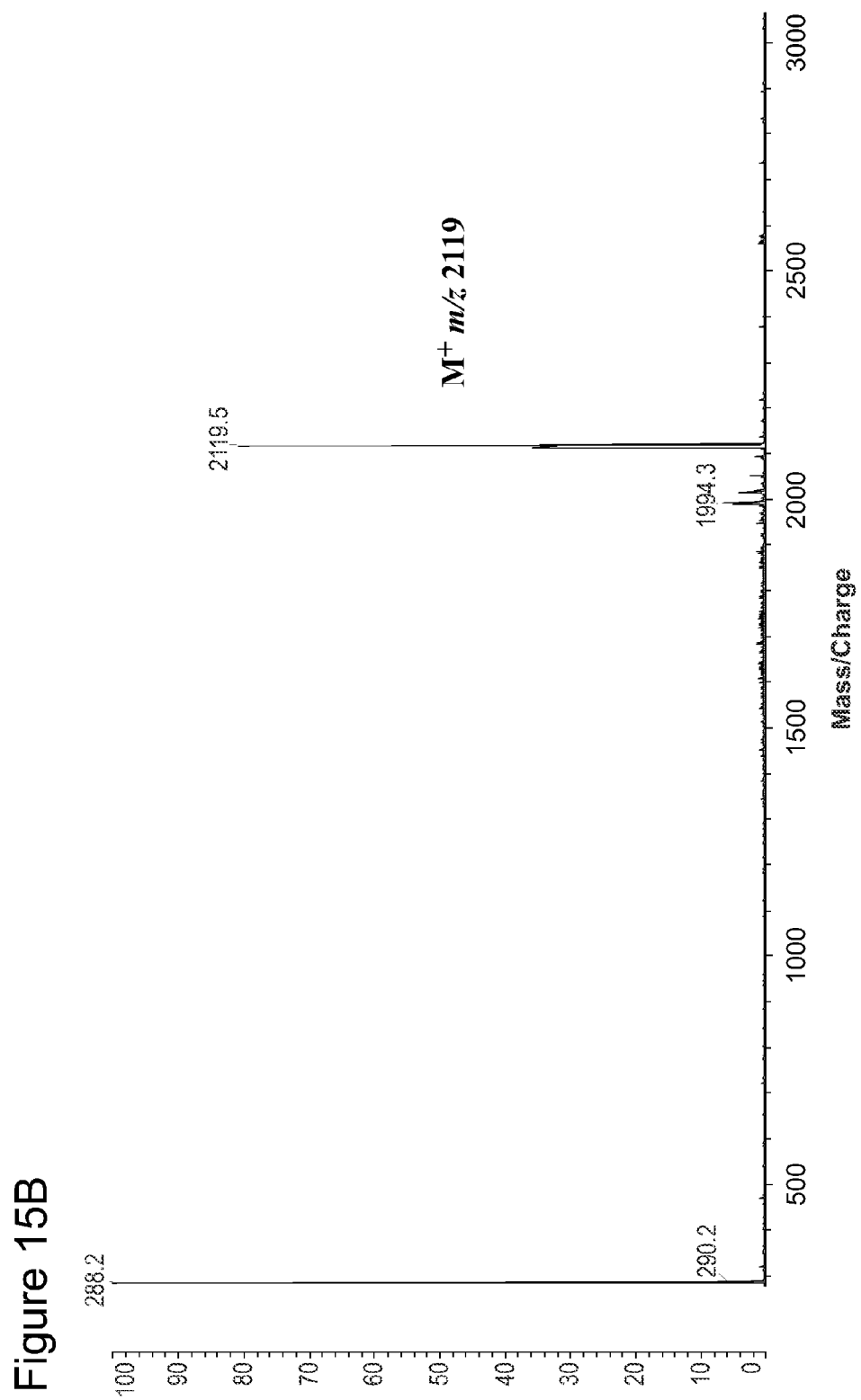

1,2,3,4,8,12,13,14,15,19-Deca(4'-t-butylphenylthio)nonacene (Compound B of FIG. 2):

To a mixture of 1,2,3,4,8,12,13,14,15,19-deca(4'-t-butylphenylthio)-6,10,17,21-tetrahydrononacene-6,10,17,21-tetraol (0.03 g, 0.014 mmol) in 1,4-dioxane (7.0 mL) was added anhydrous SnCl$_2$ (0.1 g, 0.53 mmol). To this suspension was added 10% HCl (1 mL) and the resulting mixture was stirred at room temperature for 0.5 h under Ar in complete darkness. Upon completion of the reaction, dark precipitates were filtered in the dark under a N$_2$ atmosphere. The solids were washed with water (30 mL) followed by methanol (30 mL) to yield 2 as a black solid. $^1$H NMR (500 MHz, CDCl$_3$): δ 9.37 (s, 4H), 9.08 (s, 4H), 8.65 (s, 4H), 7.12 (m, 20H), 6.98 (m, 14H), 6.85 (m, 4H), 6.73 (m, 2H), 1.20 (bs, 90H). LDI-MS m/z: 2119.84 [M$^+$], UV-vis λ$_{max}$ (nm): 532, 580, 633, 748. The $^1$H NMR spectrum and laser desorption ionization mass spectrum (LDI-MS) for 1,2,3,4,8,12,13,14,15,19-deca(4'-t-butylphenylthio)nonacene and the compound structure are shown in FIGS. 15A & B.

Figure 16A:
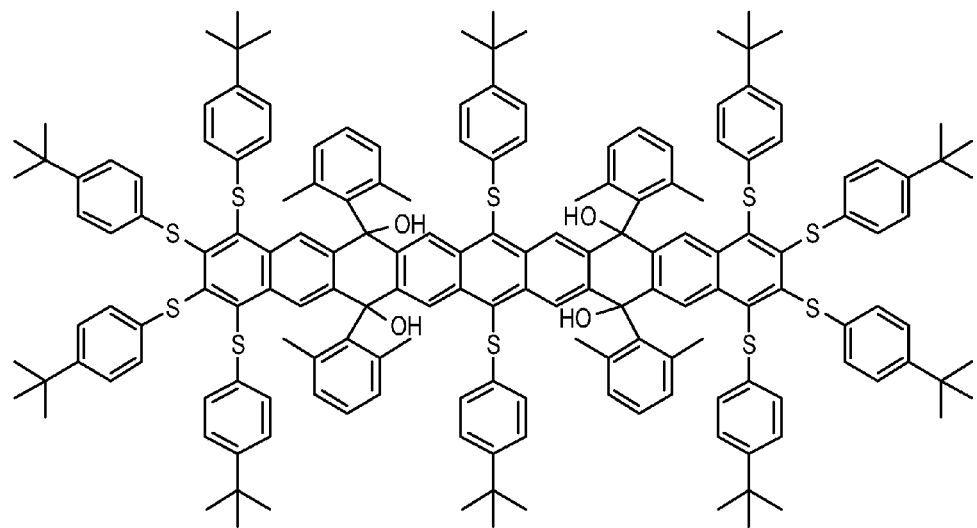
FIGS. 16A & B show the laser desorption ionization mass spectrum (LDI-MS) of 1,2,3,4,8,12,13,14,15,19-deca(4'-t-butylphenylthio)-6,10,17,21-tetrahydro-6,10,17,21-tetra(2',6'-dimethylphenyl)nonacene-6,10,17,21-tetraol (FIG. 16B). The compound structure is shown in FIG. 16A.
Figure 16B:
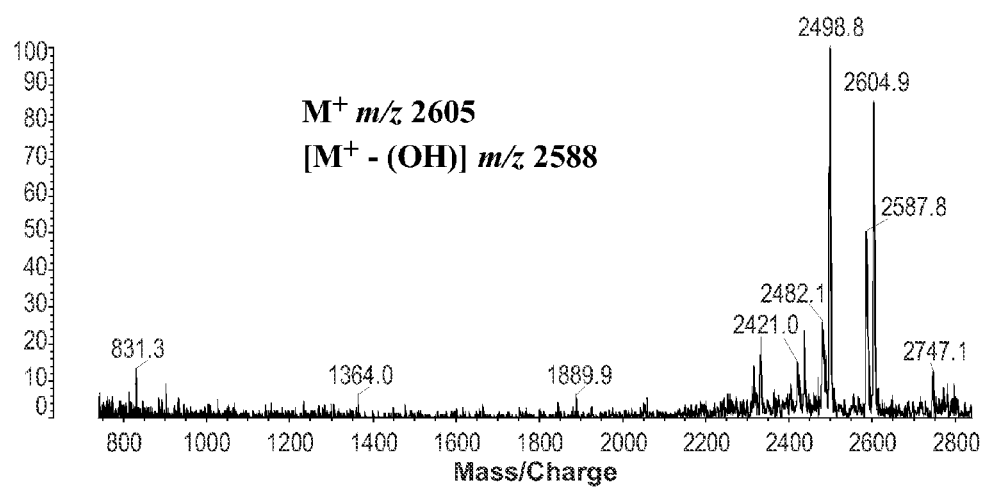

1,2,3,4,8,12,13,14,15,19-Deca(4'-t-butylphenylthio)-6,10,17,21-tetrahydro-6,10,17,21-tetra(2',6'-dimethylphenyl)nonacene-6,10,17,21-tetraol A solution of 1-bromo-2,6-dimethylbenzene (0.48 g, 2.59 mmol) was stirred in dry THF (15 mL) and cooled to −78° C. in a dry ice/acetone bath. Upon cooling, n-butyllithium (2.5 M in hexanes, 0.86 mL, 2.15 mmol) was added and the solution was stirred for 5 h at −78° C. To this pale yellow solution was added 1,2,3,4,8,12,13,14,15,19-deca(4'-t-butylphenylthio)nonacene-6,10,17,21-tetraone (0.1 g, 0.046 mmol) and the mixture was allowed to gradually warm to RT with stirring overnight. To the reaction mixture was added sat. NH$_4$Cl (10 mL). Following extraction with CH$_2$Cl$_2$ (2×20 mL), the organic layer was washed with water and dried over CaCl$_2$. The solvent was removed under vacuum until ~10 mL remained, at which point hexanes (100 mL) were added resulting in the formation of a yellow precipitate. The desired tetraol was isolated by vacuum filtration (0.09 g, 75%) and taken forward without any purification. LDI-MS m/z: 2605.10 [M$^+$], 2588.10 [M$^+$-OH]. The laser desorption ionization mass spectrum (LDI-MS) of 1,2,3,4,8,12,13,14,15,19-deca(4'-t-butylphenylthio)-6,10,17,21-tetrahydro-6,10,17,21-tetra(2',6'-dimethylphenyl)nonacene-6,10,17,21-tetraol is shown in FIG. 16B. The compound structure is shown in FIG. 16A. 1,2,3,4,8,12,13,14,15,19-deca(4'-t-butylphenylthio)-6,10,17,21-tetrahydro-6,10,17,21-tetra(2',6'-dimethylphenyl)nonacene-6,10,17,21-tetraol exposed to long wavelength UV light exhibits a yellow-orange fluorescence.

Figure 17A:
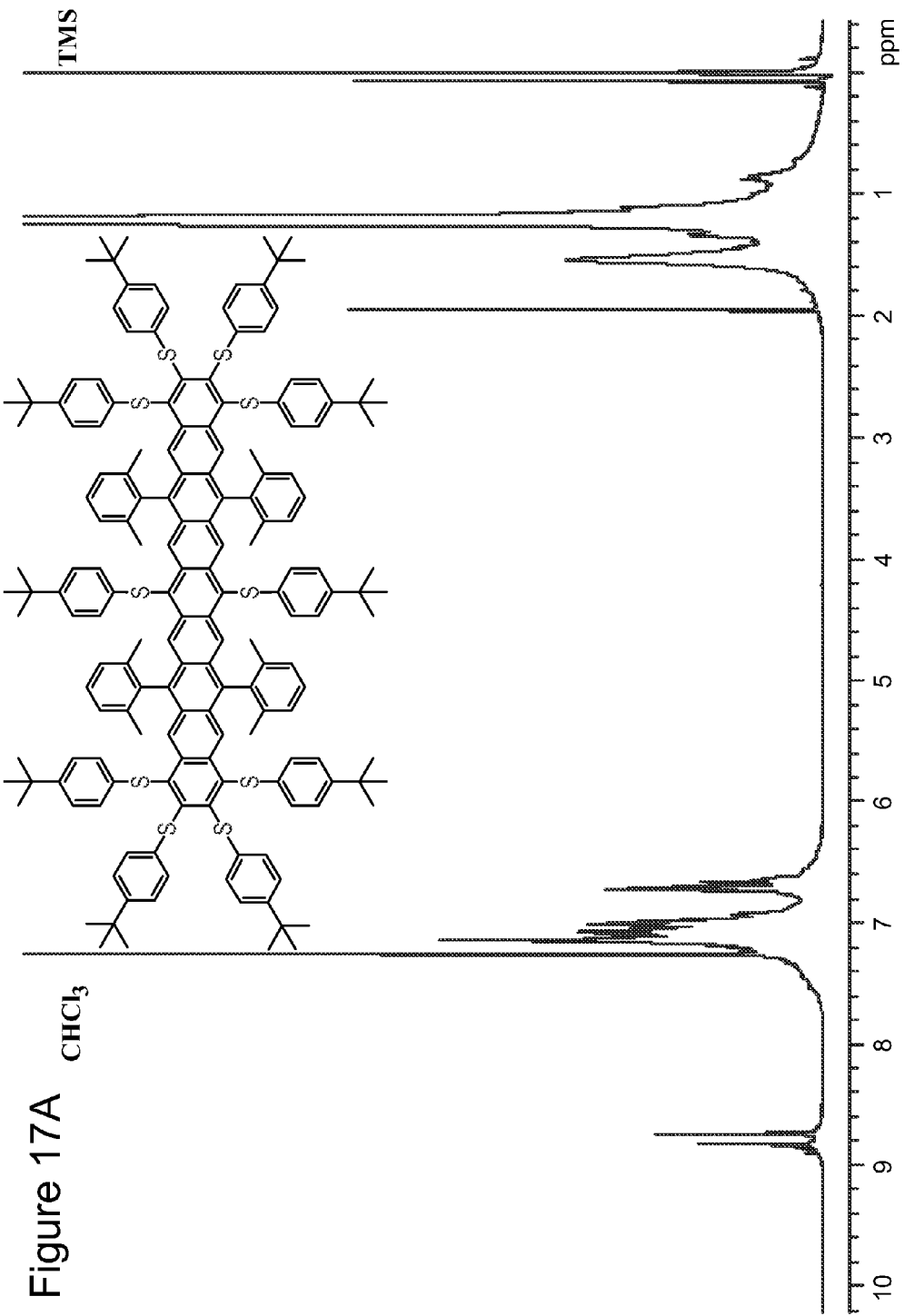
FIGS. 17A and B show the $^1$H NMR spectrum of 1,2,3,4,8,12,13,14,15,19-deca(4'-t-butylphenylthio)-6,10,17,21-tetra(2',6'-dimethylphenyl)nonacene.
Figure 17B:
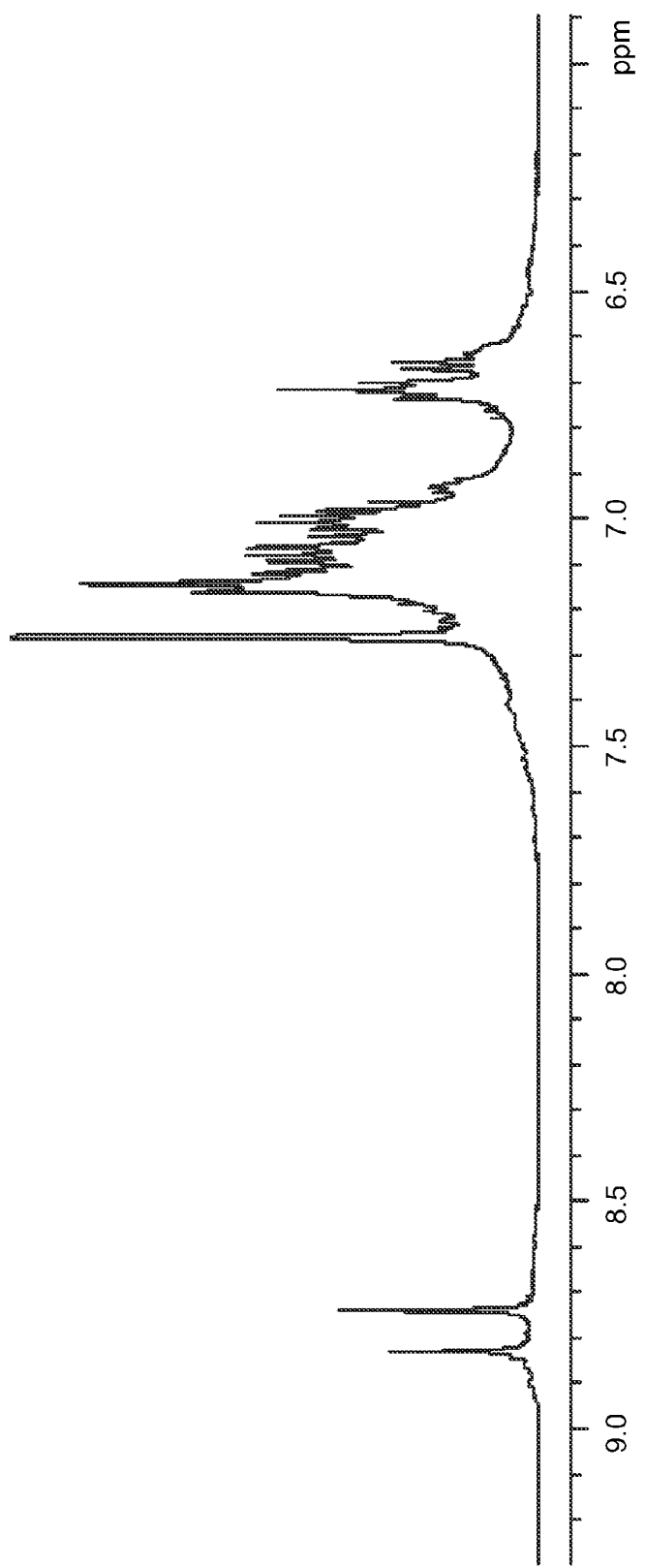
FIG. 17B shows a close-up of the section of FIG. 17A between 9.0 and 6.5 ppm. The compound structure is shown in FIG. 17A.

1,2,3,4,8,12,13,14,15,19-Deca(4'-t-butylphenylthio)-6,10,17,21-tetra(2',6'-dimethylphenyl)nonacene (Compound A of FIG. 2):

To a mixture of 1,2,3,4,8,12,13,14,15,19-deca(4'-t-butylphenylthio)-6,10,17,21-tetrahydro-6,10,17,21-tetra(2',6'-dimethylphenyl)nonacene-6,10,17,21-tetraol (0.04 g, 0.015 mmol) in 1,4-dioxane (10 mL) was added anhydrous SnCl$_2$ (0.1 g, 0.52 mmol). To this suspension was added 10% HCl (1 mL) in complete darkness and the resulting mixture was stirred at room temperature for 0.5 h under Ar. Upon completion of the reaction, black precipitates were filtered in the dark light under N$_2$. The solids were washed with water (50 mL) followed by methanol to yield persistent nonacene derivative 1,2,3,4,8,12,13,14,15,19-deca(4'-t-butylphenylthio)-6,10,17,21-tetra(2',6'-dimethylphenyl)nonacene as a black solid. $^1$H NMR (500 MHz, CDCl$_3$): δ 8.83 (s, 4H), 8.74 (s, 4H), 7.14 (m, 20H), 7.08 (m, 10H), 7.00 (m, 10H), 6.72 (m, 8H), 6.66 (m, 4H), 1.96 (s, 24H), 1.23 (bs, 90H). $^{13}$C NMR (125.68 MHz, CDCl$_3$): δ 148.9, 148.7, 148.5, 148.4, 143.5, 143.4, 142.9, 137.7, 137.1, 136.0, 134.2, 133.7, 131.4, 131.3, 130.9, 128.7, 128.4, 128.2, 128.0, 127.9, 127.5, 127.2, 126.1, 126.1, 126.0, 126.0, 34.50, 34.48, 31.51, 31.45, 31.4, 19.9. LDI-MS m/z: 2536 [M$^+$], UV-vis λ$_{max}$ (nm): 550, 600, 655, 716, 846, 921, 1033. The $^1$H NMR spectrum of 1,2,3,4,8,12,13,14,15,19-deca(4'-t-butylphenylthio)-6,10,17,21-tetra(2',6'-dimethylphenyl)nonacene and the compound structure are shown in FIGS. 17A & B.

Figure 18:
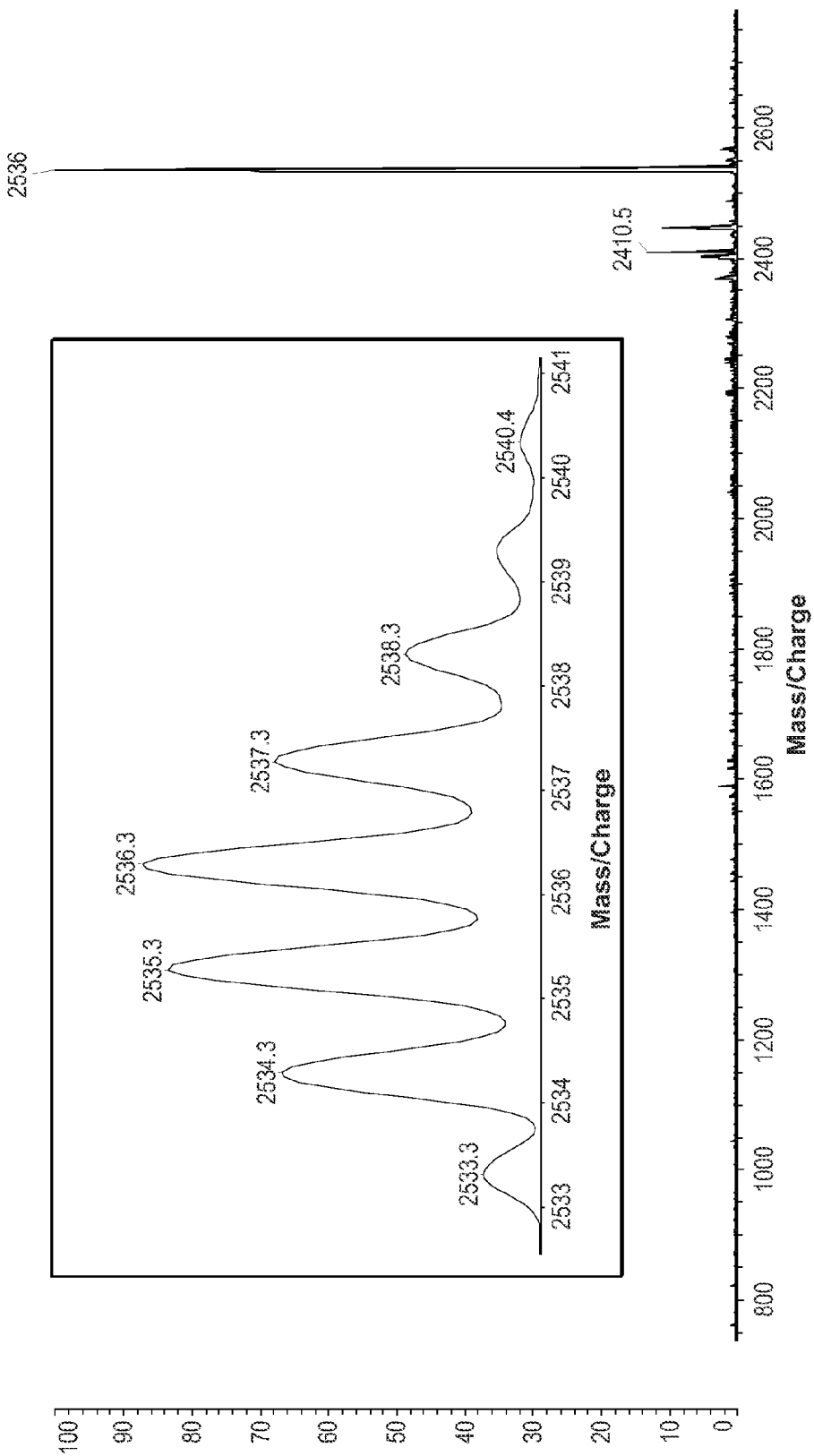
FIG. 18 shows the laser desorption ionization mass spectrum (LDI-MS) of 1,2,3,4,8,12,13,14,15,19-deca(4'-t-butylphenylthio)-6,10,17,21-tetra(2',6'-dimethylphenyl)nonacene.
Figure 19:
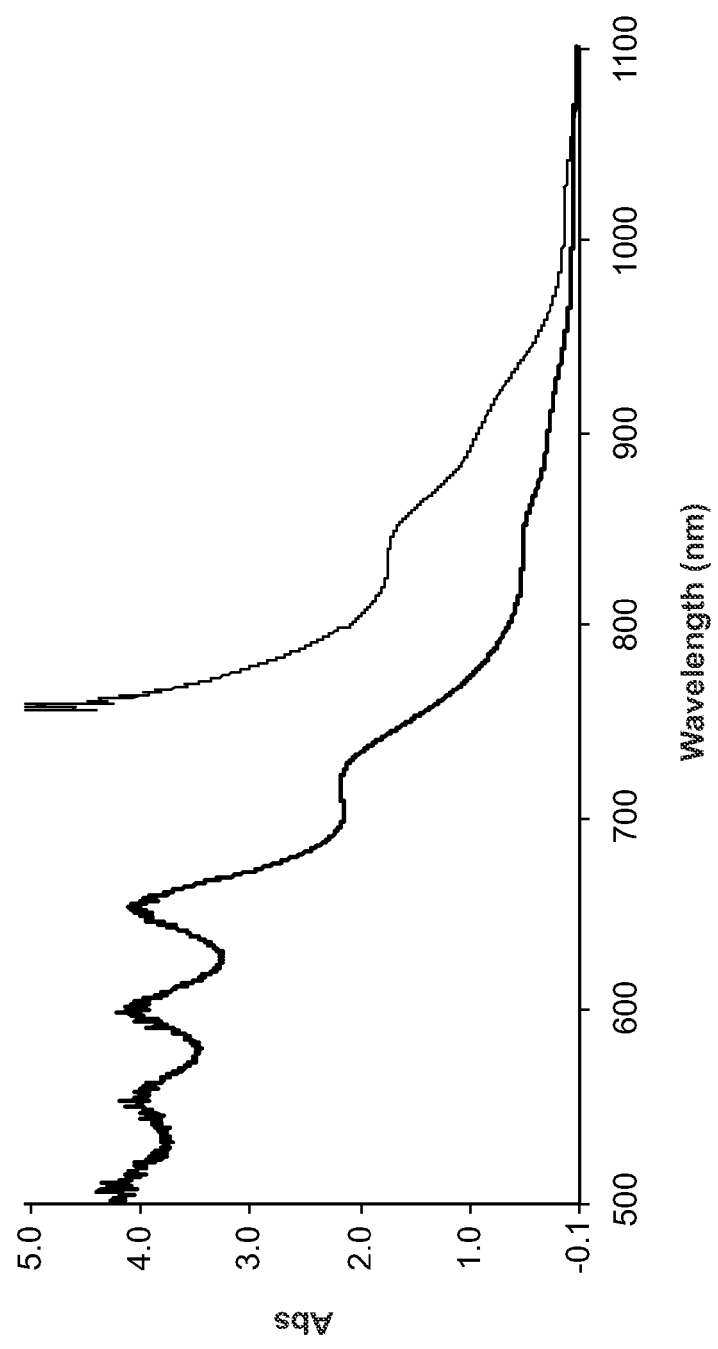
FIG. 19 shows the ultraviolet-visible-near infrared (UV-vis-NIR) spectrum of 1,2,3,4,8,12,13,14,15,19-deca(4'-t-butylphenylthio)-6,10,17,21-tetra(2',6'-dimethylphenyl)nonacene.

The laser desorption ionization mass spectrum (LDI-MS) of 1,2,3,4,8,12,13,14,15,19-deca(4'-t-butylphenylthio)-6,10,17,21-tetra(2',6'-dimethylphenyl)nonacene is shown in FIG. 18. The ultraviolet-visible-near infrared (UV-vis-NIR) spectrum of 1,2,3,4,8,12,13,14,15,19-deca(4'-t-butylphenylthio)-6,10,17,21-tetra(2',6'-dimethylphenyl)nonacene is shown In FIG. 19. 1,2,3,4,8,12,13,14,15,19-deca(4'-t -butylphenylthio)-6,10,17,21-tetra(2',6'-dimethylphenyl)nonacene appears as a black solution in room light but as a red blood solution when exposed to long wavelength UV light due to its strong, blood red fluorescence. Following air oxidation, the black solution turns brown and the color of the fluorescence changes from blood red to pale pink. 1,2,3,4,8,12,13,14,15,19-deca(4'-t-butylphenylthio)-6,10,17,21-tetra(2',6'-dimethylphenyl)nonacene dissolved in methylene chloride, placed inside a vial and exposed to long wavelength UV light shows strong, blood red fluorescence that is characteristic of this nonacene derivative.

What is claimed is:

1. A oxidatively resistant nonacene composition selected from the group consisting of:

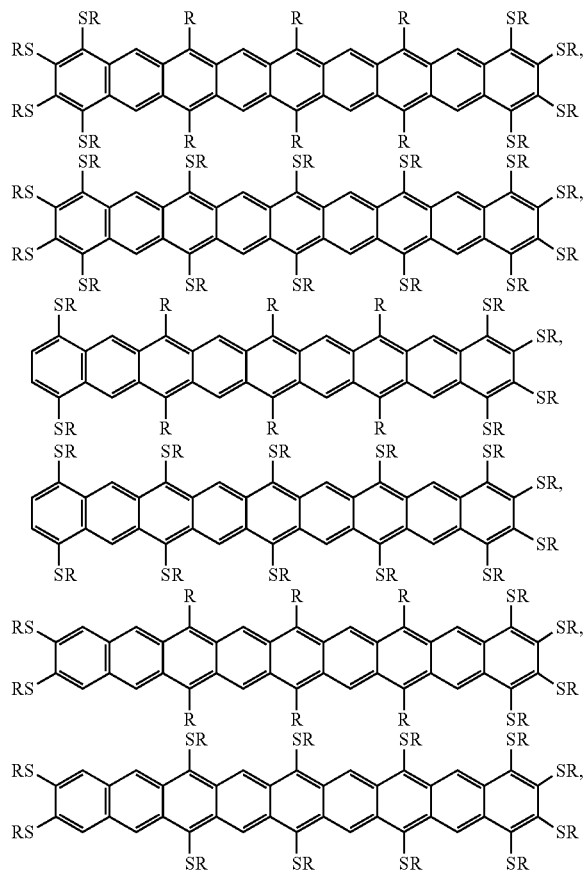

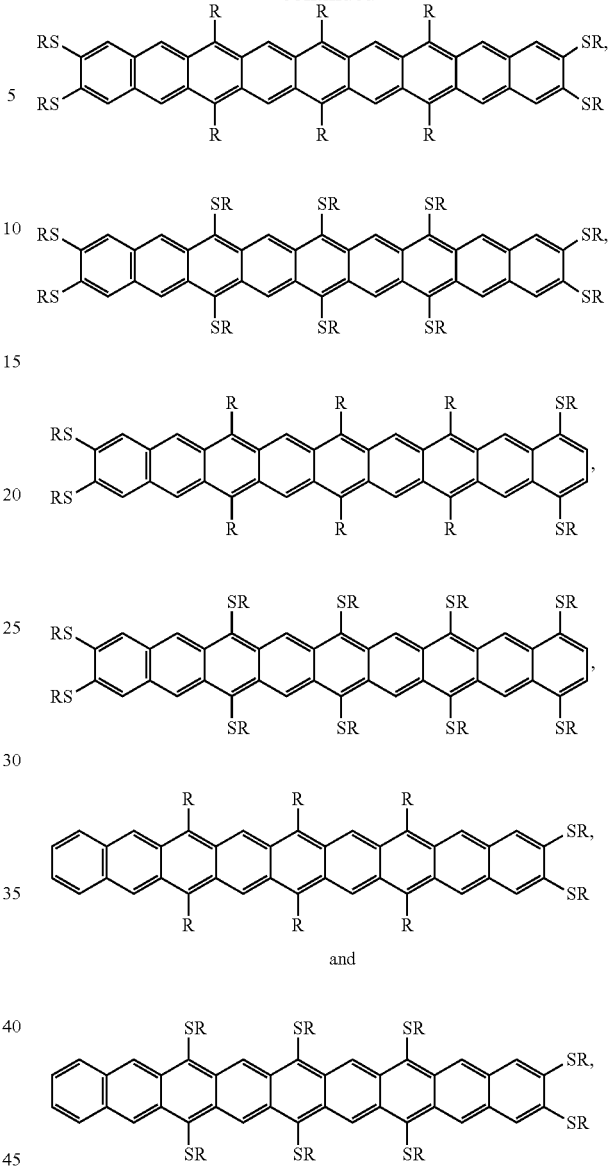

wherein R is selected from the group consisting of hydrogen, alkyl moieties, the nitrile group, the isonitrile group, carbonyl moieties, alkene moieties, alkyne moieties, trialkylsilylethynyl moieties, aromatic moieties, the trifluoromethyl group, other perfluoroalkyl moieties, halogens, alkylthio moieties, and arylthio moieties and wherein the resulting structure has a zero or approximately zero total spin, $\langle S^2 \rangle$, as calculated by density functional theory.

2. The composition of claim 1, wherein said oxidatively resistant nonacene is:

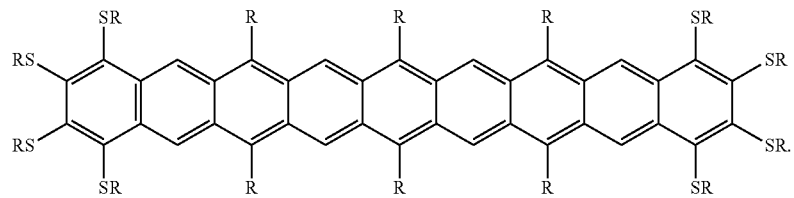

3. The composition of claim 1, wherein said oxidatively resistant nonacene is:

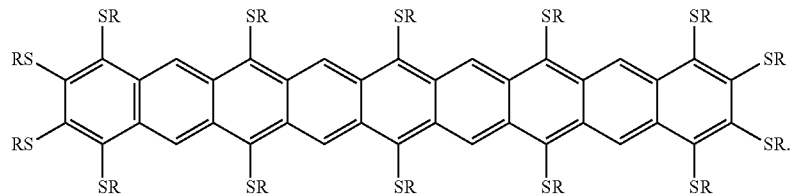

4. The composition of claim 1, wherein said oxidatively resistant nonacene is:

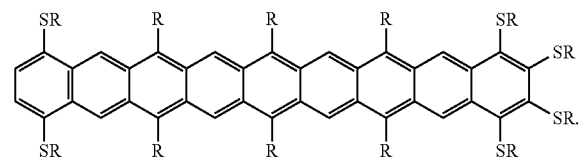

5. The composition of claim 1, wherein said oxidatively resistant nonacene is:

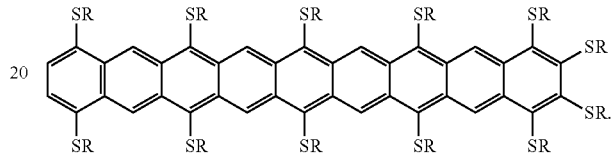

6. The composition of claim 1, wherein said oxidatively resistant nonacene is:

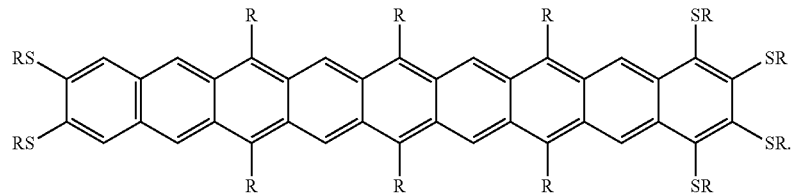

7. The composition of claim 1, wherein said oxidatively resistant nonacene is:

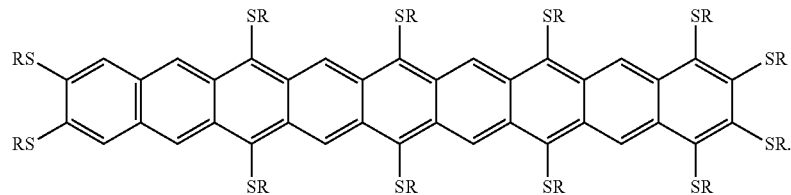

8. The composition of claim 1, wherein said oxidatively resistant nonacene is:

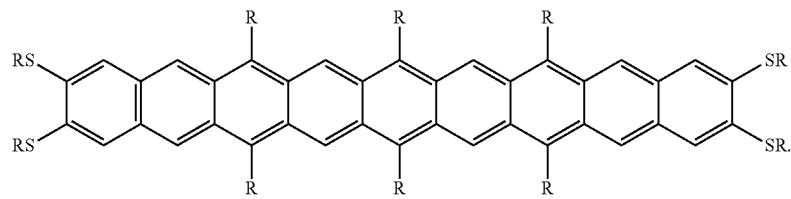

9. The composition of claim 1, wherein said oxidatively resistant nonacene is:

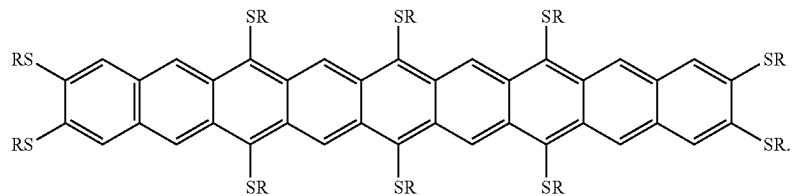

10. The composition of claim 1, wherein said oxidatively resistant nonacene is:

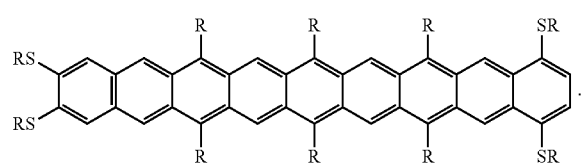

11. The composition of claim 1, wherein said oxidatively resistant nonacene is:

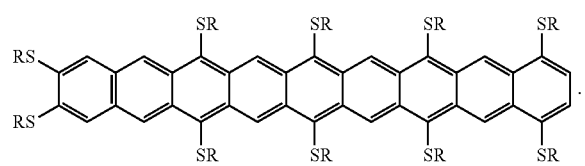

12. The composition of claim 1, wherein said oxidatively resistant nonacene is:

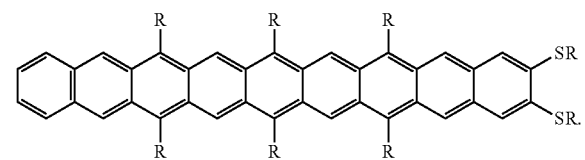

13. The composition of claim 1, wherein said oxidatively resistant nonacene is:

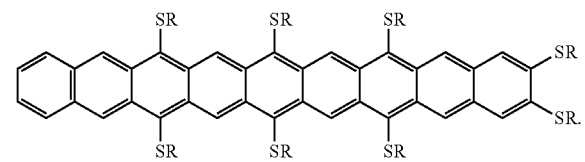

14. The composition of claim 1, wherein said oxidatively resistant nonacene is:

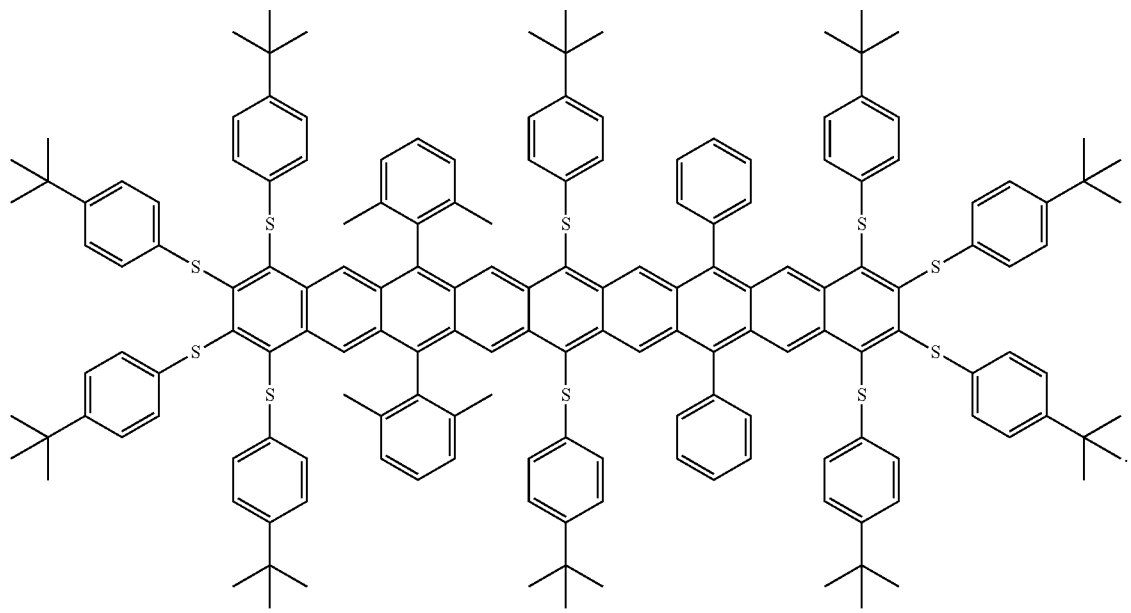 [SMILES: Cc1cccc(C)c1-c1c2cc3c(Sc4ccc(C(C)(C)C)cc4)c(Sc4ccc(C(C)(C)C)cc4)c(Sc4ccc(C(C)(C)C)cc4)c(Sc4ccc(C(C)(C)C)cc4)c3cc2c(-c2c(C)cccc2C)c2cc3c(Sc4ccc(C(C)(C)C)cc4)c4cc5c(-c6ccccc6)c6cc7c(Sc8ccc(C(C)(C)C)cc8)c(Sc8ccc(C(C)(C)C)cc8)c(Sc8ccc(C(C)(C)C)cc8)c(Sc8ccc(C(C)(C)C)cc8)c7cc6c(-c6ccccc6)c5cc4c(Sc4ccc(C(C)(C)C)cc4)c3cc12]

15. The composition of claim 1, wherein said oxidatively resistant nonacene is:
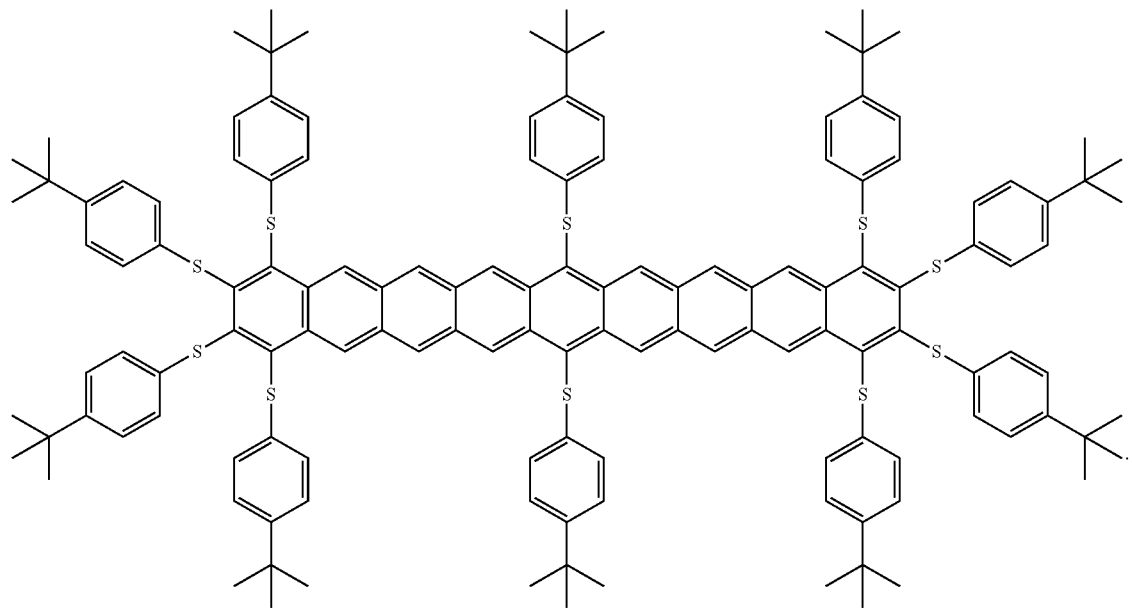 [SMILES: CC(C)(C)c1ccc(Sc2c(Sc3ccc(C(C)(C)C)cc3)c(Sc3ccc(C(C)(C)C)cc3)c3cc4cc5cc6c(Sc7ccc(C(C)(C)C)cc7)c7cc8cc9cc%10c(Sc%11ccc(C(C)(C)C)cc%11)c(Sc%11ccc(C(C)(C)C)cc%11)c(Sc%11ccc(C(C)(C)C)cc%11)c(Sc%11ccc(C(C)(C)C)cc%11)c%10cc9cc8cc7c(Sc7ccc(C(C)(C)C)cc7)c6cc5cc4cc3c2Sc2ccc(C(C)(C)C)cc2)cc1]
16. An electronic device comprising an oxidativley resistant nonacene selected from one or more of the group consisting of:
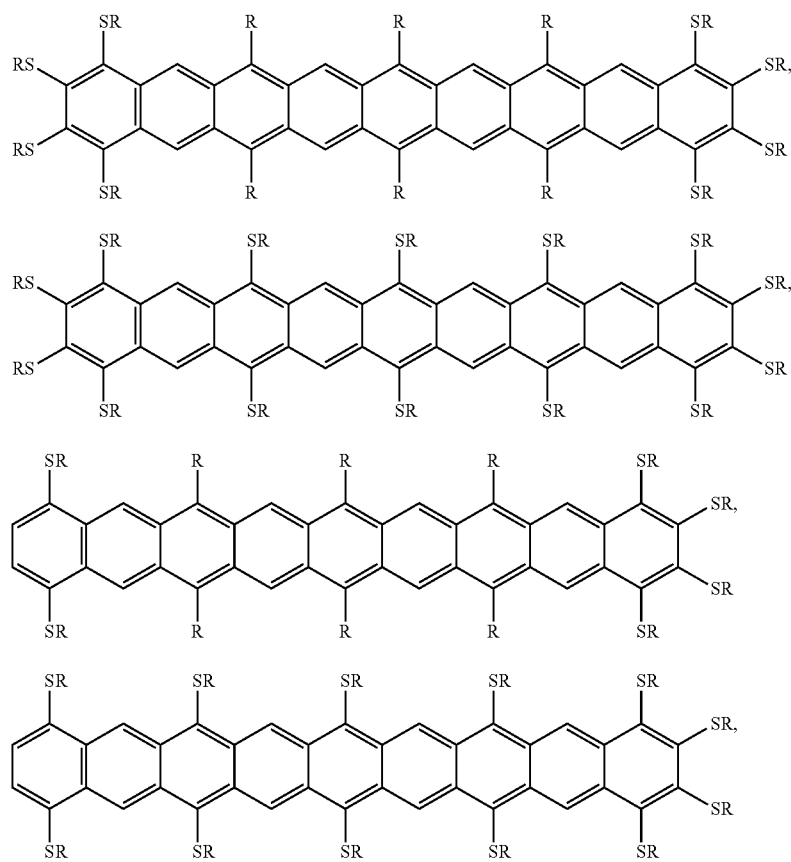

-continued

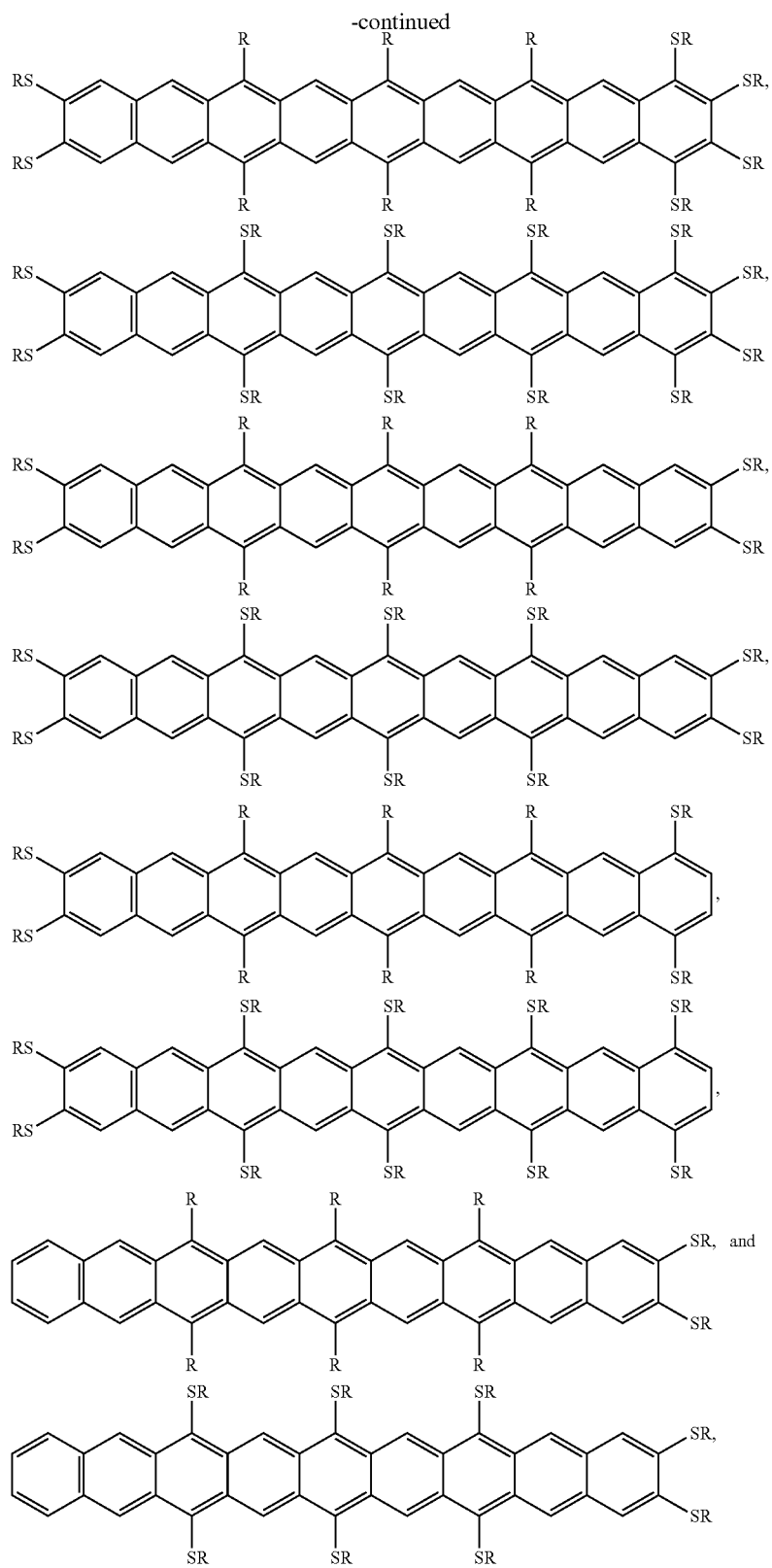

wherein R is selected from the group consisting of hydrogen, alkyl moieties, the nitrile group, the isonitrile group, carbonyl moieties, alkene moieties, alkyne moieties, trialkylsilylethynyl moieties, aromatic moieties, the trifluoromethyl group, other perfluoroalkyl moieties, halogens, alkylthio moieties, and arylthio moieties and wherein the resulting structure has a zero or approximately zero total spin, $<S^2>$, as calculated by density functional theory.

17. The electronic device of claim 16, wherein said oxidatively resistant nonacene is:

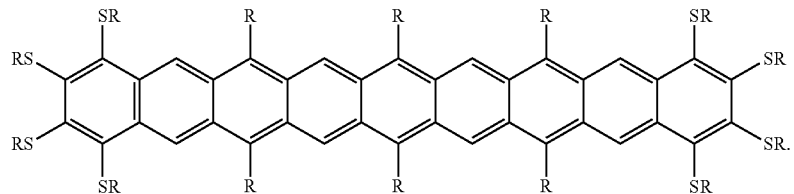

18. The electronic device of claim 16, wherein said oxidatively resistant nonacene is:

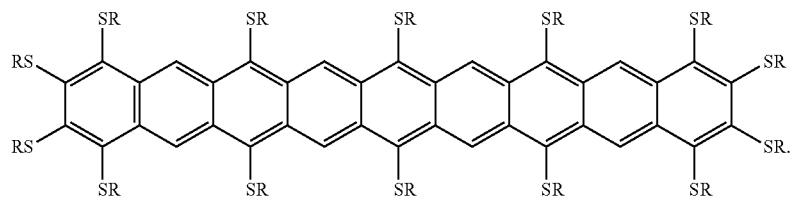

19. The electronic device of claim 16, wherein said oxidatively resistant nonacene is:

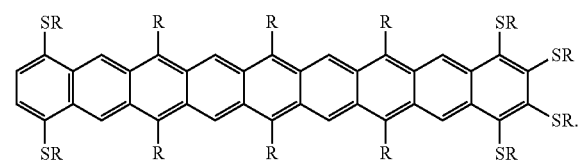

20. The electronic device of claim 16, wherein said oxidatively resistant nonacene is:

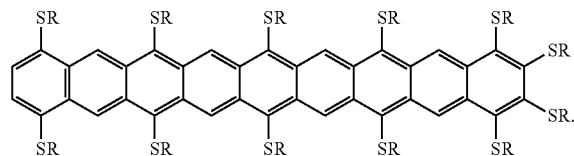

21. The electronic device of claim 16, wherein said oxidatively resistant nonacene is:

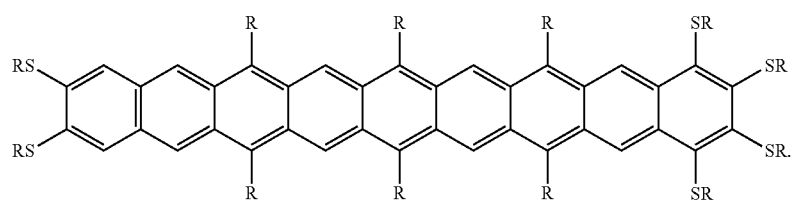

22. The electronic device of claim 16, wherein said oxidatively resistant nonacene is:

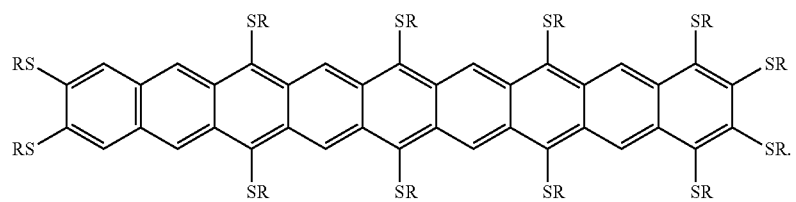

23. The electronic device of claim 16, wherein said oxidatively resistant nonacene is:

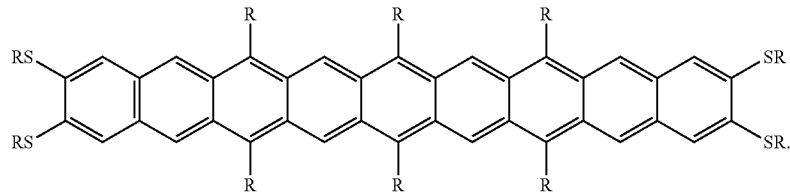

24. The electronic device of claim 16, wherein said oxidatively resistant nonacene is:

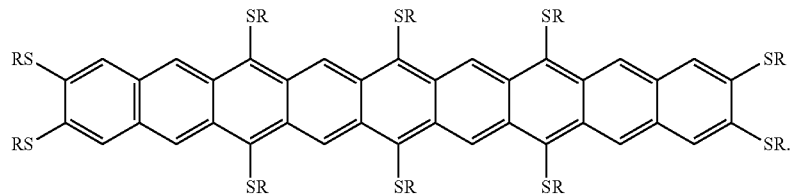

25. The electronic device of claim 16, wherein said oxidatively resistant nonacene is:

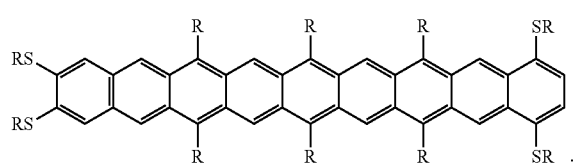

26. The electronic device of claim 16, wherein said oxidatively resistant nonacene is:

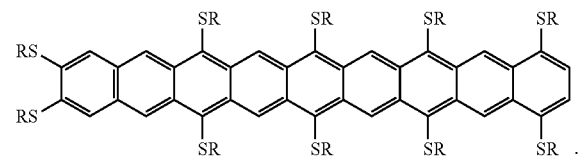

27. The electronic device of claim 16, wherein said oxidatively resistant nonacene is:

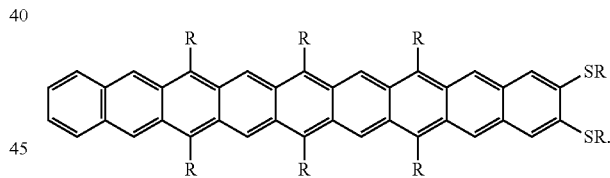

28. The electronic device of claim 16, wherein said oxidatively resistant nonacene is:

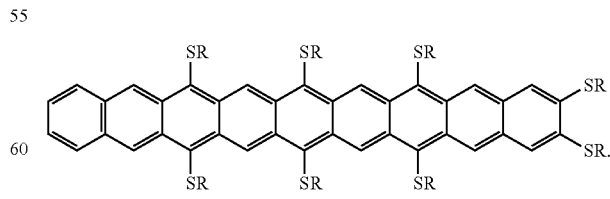

29. The electronic device of claim 16, wherein said oxidatively resistant nonacene is:

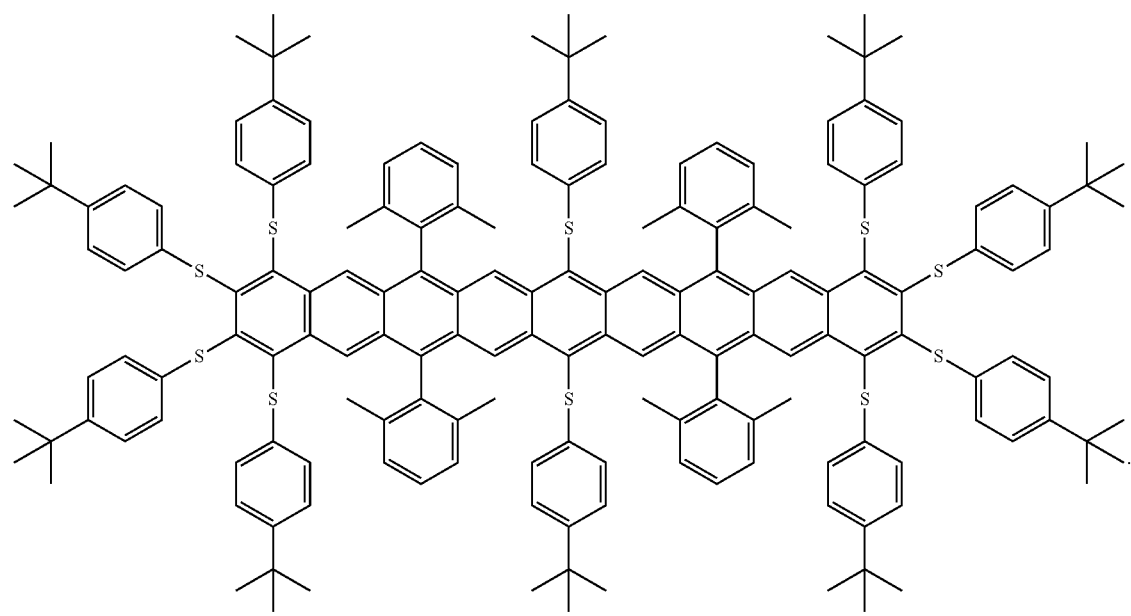 [SMILES: Cc1cccc(C)c1-c1c2cc3c(Sc4ccc(C(C)(C)C)cc4)c(Sc4ccc(C(C)(C)C)cc4)c(Sc4ccc(C(C)(C)C)cc4)c(Sc4ccc(C(C)(C)C)cc4)c3cc2c(-c2c(C)cccc2C)c2cc3c(Sc4ccc(C(C)(C)C)cc4)c4cc5c(-c6c(C)cccc6C)c6cc7c(Sc8ccc(C(C)(C)C)cc8)c(Sc8ccc(C(C)(C)C)cc8)c(Sc8ccc(C(C)(C)C)cc8)c(Sc8ccc(C(C)(C)C)cc8)c7cc6c(-c6c(C)cccc6C)c5cc4c(Sc4ccc(C(C)(C)C)cc4)c3cc12]
30. The electronic device of claim 16, wherein said oxidatively resistant nonacene is:
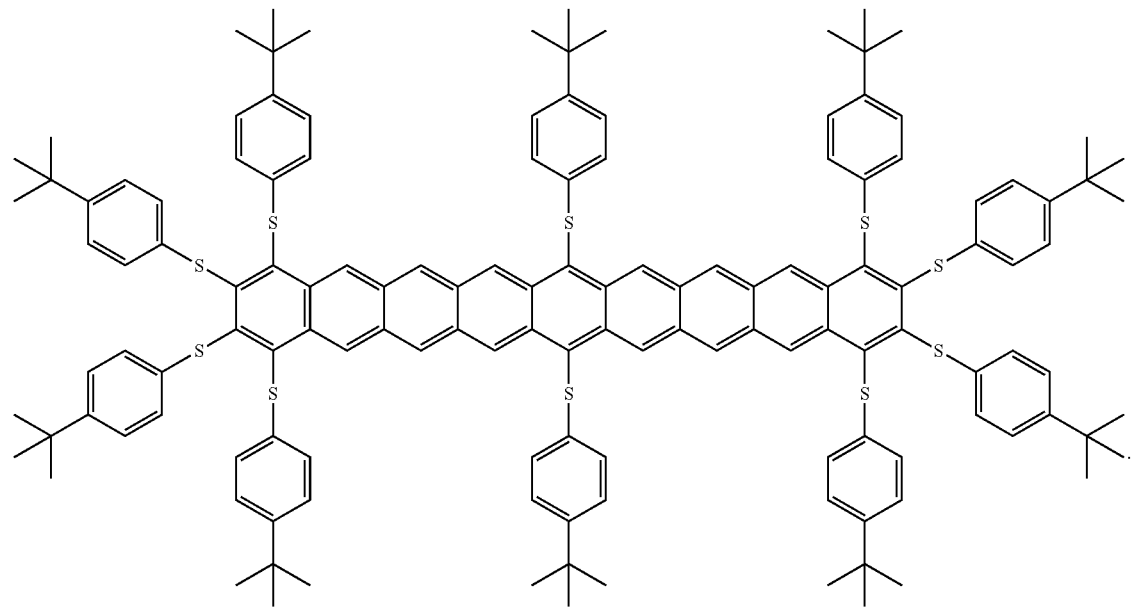 [SMILES: CC(C)(C)c1ccc(Sc2c(Sc3ccc(C(C)(C)C)cc3)c(Sc3ccc(C(C)(C)C)cc3)c3cc4cc5cc6c(Sc7ccc(C(C)(C)C)cc7)c7cc8cc9cc%10c(Sc%11ccc(C(C)(C)C)cc%11)c(Sc%11ccc(C(C)(C)C)cc%11)c(Sc%11ccc(C(C)(C)C)cc%11)c(Sc%11ccc(C(C)(C)C)cc%11)c%10cc9cc8cc7c(Sc7ccc(C(C)(C)C)cc7)c6cc5cc4cc3c2Sc2ccc(C(C)(C)C)cc2)cc1]
* * * * *